United States Patent
Ranson et al.

(10) Patent No.: US 7,547,441 B2
(45) Date of Patent: Jun. 16, 2009

(54) PAI-2 CONJUGATES FOR THE TREATMENT AND IMAGING OF CANCER

(75) Inventors: Marie Ranson, Austinmer (AU); Barry John Allen, Yowie Bay (AU); Clive Leighton Bunn, West Ryde (AU)

(73) Assignees: PAI-2 Pty Limited, Thornleigh (AU); University of Wollongong, Gwynneville (AU); Medical Scitec Australia Pty Ltd, Yowie Bay (AU)

( * ) Notice: Subject to any disclaimer, the term of this patent is extended or adjusted under 35 U.S.C. 154(b) by 1696 days.

(21) Appl. No.: 09/790,900

(22) Filed: Feb. 23, 2001

(65) Prior Publication Data

US 2002/0002134 A1    Jan. 3, 2002

(30) Foreign Application Priority Data

Feb. 24, 2000    (AU)    .................................... PQ5824

(51) Int. Cl.
*A61K 39/385* (2006.01)
*A61K 35/58* (2006.01)
*C12Q 1/26* (2006.01)
*C12N 5/06* (2006.01)
*C12N 5/00* (2006.01)
*G01N 23/00* (2006.01)
*G01N 33/48* (2006.01)

(52) U.S. Cl. ............ 424/194.1; 424/193.1; 424/196.11; 424/197.11; 424/542; 435/26; 435/326; 435/346; 436/57; 436/64; 436/86; 436/164; 436/166; 436/172; 514/1; 514/2; 514/4

(58) Field of Classification Search .................... 514/1, 514/2, 4; 530/300, 350; 424/193.1, 197.11, 424/542, 194.1, 196.11; 435/326, 346, 240.26, 435/240.27, 26; 436/57, 64, 86, 164, 166, 436/172

See application file for complete search history.

(56) References Cited

U.S. PATENT DOCUMENTS

| | | | |
|---|---|---|---|
| 5,124,471 A * | 6/1992 | Gansow et al. | |
| 5,422,090 A | 6/1995 | Stephens et al. | |
| 5,679,350 A | 10/1997 | Jankun et al. | ............ 424/193.1 |
| 6,348,185 B1 * | 2/2002 | Piwnica-Worms | |

OTHER PUBLICATIONS

Lazar, Eliane et al. Transforming Growth factor alpha: mutation of aspartic acid 47 and leucine 48 results in different biological activities, Molecular and Cellular 8(3): 1247-1252, Mar. 1988.*

Tsatas et al. Tissue-specific expression of the relaxed conformation of plasminogen activator inhibitor-2 and low-density lipoprotein receptor-related protein in human term gestational tissues. The Journal of Histochemistry and Cytochemistry 45(12): 1593-1602, 1997.*

Conese and Blasi. Urokinase/Urokinase Receptor System: internalization/degradation of urokinase-serpin complexes: mechanism and regulation. Biol. Chem. Hoppe-Seyler 376: 143-155, Mar. 1995.*

Ye et al., "cDNA Cloning and Expression in *Escherichia coli* of a Plasminogen Activator Inhibitor from Human Placenta", Journal of Biological Chemistry, vol. 262 (8): 3718-3725 (Mar. 15, 1987).

Antalis et al.; Cloning and expression of a cDNA coding for a human monocyte-derived plasminogen activator inhibitor, Proc. Natl. Acad. Sci. USA, vol. 85: 985-989 (Feb. 1988).

Jensen et al., Type-2 plasminogen-activator inhibitor is a substrate for trophoblast transglutaminase and Factor $XIII_a$; Transglutaminase-catalyzed cross-linking to cellular and extracellular structures, Eur. J. Biochem., 214: 141-146 (1993).

Saunders et al., Immunological Detection of Conformational Neoepitopes Associated with the Serpin Activity of Plasminogen Activator Inhibitor Type-2, Journal of Biological Chemistry, vol. 273 (18): 10965-10971 (May 1, 1998).

Ragno et al., Urokinase-type plasminogen activator/type-2 plasminogen-activator inhibitor complexes are not internalized upon binding to the urokinase-type-plasminogen-activator receptor in THP-1 cells, Eur. J. Biochem., 233: 514-519 (1995).

Schmitt et al., The urokinase plasminogen activator system as a novel target for tumor therapy, Fibrinolysis & Proteolysis, 14(2/3): 114-132 (2000).

Hermans et al., Inhibition of Acrosin by Serpins, A Suicide Substrate Mechanism, Biochemistry, 34: 3678-3685 (1995).

Jankova et al., Crystal Structure of the Complex of Plasminogen Activator Inhibitor 2 with a Peptide Mimicking the Reactive Center Loop, Journal of Biological Chemistry, vol. 276 (46): 43374-43382 (Nov. 16, 2001).

Andronicos et al., The human ENO1 gene product (recombinant human α-enolase) displays characteristics required for a plasminogen binding protein, Biochimica et Biophysica Acta 1337: 27-39 (1997).

Saunders et al., Interaction between the P14 Residue and Strand 2 of β-Sheet B Is Critical for Reactive Center Loop Insertion in Plasminogen Activator Inhibitor-2, Journal of Biological Chemistry, vol. 276 (46): 43383-43389 (Nov. 16, 2001).

Jensen et al., Lysosomal degradation of receptor-bound urokinase-type plasminogen activator is enhanced by its inhibitors in human trophoblastic choriocarcinoma cells, Cell Regulation, vol. 1, 1043-1056 (Dec. 1990).

Hermanson, Bioconjugate Techniques, Bifunctional Chelating Agents and Radioimmunoconjugates, 365 (Academic Press 1996).

International Search Report, Mar. 9, 2004.

B.J. Allen et al., "In vitro and preclinical targeted alpha therapy for melanoma, breast, prostate and colorectal cancers", Critical Reviews in Oncology/Hematology, Elsevier Science Ireland Ltd., Limerick, Ireland, vol. 39, No. 1-2, Jul. 2001, pp. 139-146.

B.J. Allen et al., "Targeted alpha therapy: Evidence for potential efficacy of alpha-immunoconjugates in the management of micrometastatic cancer", Australasian Radiology, Blackwell Science Ltd., AU, vol. 43, 1999, pp. 480-486.

(Continued)

*Primary Examiner*—Alana M. Harris
(74) *Attorney, Agent, or Firm*—Foley & Lardner LLP

(57) ABSTRACT

A method is described for detecting, visualizing, or treating cells, particularly cancerous cells, that express a uPA/uPAR complex. The method employs a PAI-2 conjugate molecule that comprises PAI-2 or a functional derivative, homologue, analogue, chemical equivalent or mimetic thereof, which PAI-2 is bound, linked, or otherwise associated with a toxin or label.

17 Claims, 15 Drawing Sheets

OTHER PUBLICATIONS

Jean Maublant, "Scintigraphic imaging of breast tumors", European Journal of Radiology, Ireland Jan.I 1997, vol. 24, No. 1/1997, pp. 2-10.

B.J. Allen et al., Alpha- and beta-emitting radiolanthanides in targeted cancer therapy: The potential role of terbium-149, Nuclear Medicine Communications, © 1996 Chapman and Hall Ltd., pp. 40-47, (1996).

B.J. Allen et al., "Can alpha-immunotherapy succeed where other systemic modalities have failed?", Nuclear Medicine Communications (20), © 1999 Lippincott Williams & Wilkins, pp. 205-207, (1999).

Peter A. Andreasen et al., "The Urokinase-Type Plasminogen Activator System in Cancer Metastasis: a Review", Int. J. Cancer: 72, © 1977 Wiley-Liss, Inc., pp. 1-22, (1977).

Duffy, Michael J. et al., "Urokinase Plasminogen Activator: A Prognostic Mqrker in Multiple in Multiple Types of Cancer", Journal of Surgical Oncology (71), © 1999 Wiley-Liss, Inc., pp. 130-135, (1999).

Foekens, John A. et al., Plasminogen Activator Inhibitor-2: Prognostic Relevance in 1012 Patients with Primary Breast Cancer[1], Cancer Research (55), pp. 1423-1427, (Apr. 1, 1995).

Hang, M.T.N., et al., "Pharmacokinetics and biodistribution of recombinant human plasminogen activator inhibitor type 2 (PAI-2) in control an dtumor xenograft-bearing mice", Fibrinolysis & Proteolysis 12(3), © Harcurt Brace & Co., Ltd., pp. 145-154, (1998).

Jankun, Jerzy et al., "Antitumor Activity of the Type 1 Plasminogen Activator Inhibitor Cytotixic Conjugate in Vitro1," Advances in Brief, PAI-2 Project, pp. 5829-5832, Oct. 15, 1992.

Kennel, SJ et al., "Radioimmunotherapy of micrometastases in lung with vascular targeted $^{213}$Bi", British Journal of Cancer 80(1/2), © 1999 Cancer Reserach Campaign, pp. 175-184, (1999).

Kruithof, Egbert K.O., "Biological and Clinical Aspects of Plasminogen Activitor Inhibitor Type 2", Blood vol. 86, No. 11, © 1995 The American Society of Hematology, pp. 4007-4024, (Dec. 1, 1995).

Laug, Walter E. et al., Inhibition of Invasion of HT1080 Sarcoma Cells Expressing recmbinant Plasminogen Activator Inhibitor 2[1], Cancer Research 53, pp. 6051-6057, (Dec. 15, 1993).

Lloyd, E.L. et al., "Cell survival following multiple-track alpha particle irradiation", Int. J. Radiat. Biol. vol. 35, No. 1, pp. 23-31, (1979).

Mueller, Barbara M. et al., "Overexpression of plasminogen activator inhibitor 2 in human melanoma cells inhibits spontaneous metastasis in *scid/scid* mice", Proc. Natl. Acad. Sci. USA 92, pp. 205-209, (Jan. 1995).

Poellaenen, Jari et al., "Directed Plasminogen Activation at the Surface of Normal and Malignant Cells", Advances in Cancer Research, vol. 57, © 1991 Academic Press, Inc., pp. 273-328.

Ranson, M. et al., "Increased plasminogen binding is associated with metastativc breast cancer cells: differential expression of plasminogen binding proteins", © 1998 Cancer Research Campaign, pp. 1586-1597.

Schmitt, M. et al., "Clinical Impact of the Plasminogen Activation System in Tumor Invasion and Metastasis: Prognostic Relevance and Target for Therapy", Thrombosis and Haemostasis 78(1), © F.K. Schattauer Verlagsgesellschaft mbH, pp. 285-296, (1997).

Yang, Jia-Lin et al., "Urokinase-Type Plasminogen Activator and its Receptor in Cololrectal Cancer: Independent Prognostic Factors of Metastasis and Cancer-Specific Survival and Potential Therapeutic Targets", Int. J. Cancer (Pred. Oncol.) 89, pp. 431-439, (2000).

\* cited by examiner

| Control and treatment | Mice number | | | | | Incidence of LN metastases |
| --- | --- | --- | --- | --- | --- | --- |
|  | 1 | 2 | 3 | 4 | 5 |  |
| Buffer | (+) | (+) | (+) | (+) | (+) | 5/5 |
| PAI 3.0 mCi/Kg | (-) | (+) | (-) | (-) | (-) | 1/5 |
| PAI 6.0 mCi/Kg | (-) | (-) | (-) | (-) | (-) | 0/5 |

| Control and treatment | Mice number | | | | | Incidence of LN metastases |
|---|---|---|---|---|---|---|
| | 1 | 2 | 3 | 4 | 5 | |
| Buffer | (+) | (+) | (+) | (+) | (+) | 5/5 |
| PAI 3.0 mCi/Kg | (-) | (+) | (-) | (-) | (+) | 2/5 |
| PAI 6.0 mCi/Kg | (-) | (-) | (+) | (-) | (-) | 1/5 |

PAI-2 CONJUGATES FOR THE TREATMENT AND IMAGING OF CANCER

TECHNICAL FIELD

The present invention relates to a method of treating a condition in a mammal, which condition is characterized by the undesirable, detrimental or otherwise unwanted growth of uPAR expressing cells and agents useful for same. More particularly, the present invention contemplates a method of treating said condition by specifically targeting the subject cells utilizing plasminogen activator inhibitor or functional derivative, equivalent, homologue, analogue or mimetic thereof coupled to a toxin such as an alpha particle emitting radioisotope. The method of the present invention is useful, inter alia, in the targeted treatment of conditions such as neoplasms and, in particular, metastatic cancers. The invention also relates to toxin labeled plasminogen activator inhibitor molecules, pharmaceutical compositions comprising same and methods for their manufacture. The invention further relates to the detection or visualization of tumors with labeled plasminogen activator inhibitor molecules.

BACKGROUND ART

Note: Bibliographic details of the publications referred to by author in this specification are collected at the end of the description.

The acquisition of the malignant phenotype involves a number of initiation and progression factors linked together in a multi-step process (Meyer and Hart 1998; Haber and Fearon, 1998). Malignant tumors are potentially lethal because of the ability of cells within the tumor to invade and spread (metastasize) throughout the body (Meyer and Hart 1998). The process of metastasis can be summarized in the following steps; escape of tumor cells from a primary tumor mass and invasion into surrounding histologically normal tissue, intravasation and extravasation (entry into and exit from the vasculature or lymphatic system), and growth and survival (via angiogenesis) of tumor cells at a secondary site. One of the major failures in the treatment of cancer is poor detection and eradication of metastases before vital organ functions are compromised, resulting in minimal long-term survival benefit (Allen, 1999). Thus, effective cancer treatment entails primary tumor resection followed by removal of all metastases arising from the primary. The latter would require (1) identification of a marker specific to metastatic cells, and (2) development of a ligand that can be used to specifically target and kill the cells expressing the marker.

Proteolytic enzymes such as urokinase plasminogen activator (herein referred to as "uPA") play a role in tumor angiogenesis and metastatic cell migration; both of which are processes that require tissue barriers to be breached (reviewed in Andreasen et al., 1997). Under normal physiological conditions, most cells express very little or no uPA (Pollanen et al., 1991). Urokinase plasminogen activator converts zymogen plasminogen into the highly active protease plasmin, which has broad specificity towards integral extracellular matrix (ECM) molecules (eg: type IV collagen, vitronectin, proteoglycan, fibronectin and laminin) (Pollanen et al., 1991). Plasmin also contributes to ECM remodeling by activating zymogen metalloproteases (MMPs) which more thoroughly degrade the collagen structural components (Pollanen et al., 1991). While plasminogen can also be converted to plasmin by tissue plasminogen activator (tPA), tPA is primarily responsible for fibronolysis (Lijnen and Collen, 1982; Pollanen et al., 1991). In contrast uPA is primarily involved in pericellular proteolysis as it binds to its specific cell-surface receptor uPAR (Pollanen et al., 1991). The activities of uPA and plasmin are physiologically inhibited by the serpins plasminogen activator inhibitors type 1 and 2 (PAI-1 and PAI-2) and alpha 2-antiplasmin, respectively (Pollanen et al., 1991). The uPA system and MMPs, such as MMP-9, have been shown to act cooperatively in allowing tumor cells to breach the vascular wall (Kim et al., 1999).

Prior art "magic bullet" style treatments for neoplastic conditions have been extensively investigated but, to date, have met with little or no success.

Specifically, most previous attempts at such targeted treatment have relied on the use of antibodies directed to various cell surface molecules expressed by cancer cells. However, such approaches have suffered from many drawbacks including:

(i) the surface molecules to which the antibodies are directed have not been uniquely expressed by the cancer cells. Accordingly, such treatments have also been toxic to a significant number of normal cells.

(ii) the antibodies which have been utilized in such treatments have been of mouse origin or have been "humanized mouse antibodies. The use of such antibodies has led to immunological complications associated with the HAMA response. That is, repeated dosing of humans with murine antibodies, such as humanized antibodies, has led to the development of anti-murine antibodies thereby causing both rapid clearance of the murine antibodies and the production of immune complexes which cause the HAMA response.

(iii) the antibody-cell surface molecule complexes are often internalized. Accordingly, the toxin which is coupled to the subject antibody is less effective.

(iv) the strength of binding of most antibodies to a target cell surface molecule is low with a dissociation constant of approximately $10^{-6}$ M being common.

(v) in coupling a toxin to the antibody the point of linkage cannot usually be predicted. Depending on the structure of a given antibody, coupling may occur at the antigen binding site region of the antibody thereby rendering the antibody useless.

Further, prior art radiocolloid therapy is not suitable for adjunctive therapy as it is not selective of cancer cells. To the extent that beta and gamma emitting radionuclides have been coupled to specific monoclonal antibodies, problems have been experienced with most of the dose leaving the cancer cell. Therefore, therapeutic doses cannot be achieved without inducing severe complications.

Accordingly, there is a need to develop a more effective method of targeting neoplastic cells for treatment, which method provides both improved selectivity in terms of its targeting function and improved delivery of a toxic signal. In terms of the delivery of a toxic signal, there is a need to develop a method which provides both a maximal dose of the subject toxin to the target cell but with minimal impact upon proximally located non-target cells.

SUMMARY OF THE INVENTION

In work leading up to the present invention the inventors have determined that plasminogen activator inhibitors (herein referred to as "PAI") and in particular PAI-2, can be used as a targeting molecule for specific delivery of a toxin since cancer cells express the uPA/uPAR complex while non-diseased cells express little or no uPA/uPAR complex. Further, the inventors have determined that the coupling of an alpha particle emitting radioisotope to PAI-2 does not inhibit binding of PAI-2 to uPA and still further, that the labeled PAI-2-uPA/uPAR complex is internalized by the targeted cell thereby providing maximal impact of the high energy radioactive emission on the target cell and minimal impact on proximal cells. This is due to the alpha-emitter being highly toxic over a short range only. Finally, unlike the observed dissociation constant of $10^{-6}$ M with respect to antibody/antigen interactions, coupling of PAI-2 to uPA is extremely strong, exhibiting a dissociation constant in the order of $10^{-11}$ M, thereby minimizing dissociation of the radiolabelled PAI-2 and consequently decreasing the risk of a toxic impact on localized non-target cells.

Accordingly, a first aspect of the present invention is directed to a method of treating a condition in a mammal, which condition is characterized by the undesirable, detrimental or otherwise unwanted growth of cells expressing a uPA/uPAR complex, said method comprising administering to said mammal an effective amount of PAI or functional derivative, equivalent, homologue, analogue or mimetic thereof, which PAI is bound, linked or otherwise associated with a toxin, for a time and under conditions sufficient to down-regulate the growth of said cells.

In a particularly preferred embodiment the plasminogen activator inhibitor (PAI) is PAI-2.

Preferably the toxin is a radioisotope, and more preferably is an alpha particle emitting radioisotope which includes, but is not limited to, Tb-149 or Bi-213. More preferably the alpha particle emitting radioisotope is Bi-213.

In a preferred embodiment the subject cell growth is proliferation, and the subject down-regulation is killing off the proliferating cells. The condition being treated is preferably cancer, more preferably a metastatic cancer which includes, but is not limited to, breast cancer, prostatic cancer and/or colorectal cancer.

According to a second aspect the present invention contemplates a method of down-regulating the growth of cells expressing a uPA/uPAR complex, said method comprising contacting said cells with an effective amount of PAI or functional derivative, equivalent, homologue, analogue or mimetic thereof, which PAI is bound, linked or otherwise associated with a toxin. In a particularly preferred embodiment said PAI is PAI-2, while said toxin is preferably an alpha particle emitting radioisotope.

In a preferred embodiment the subject cell growth is proliferation, and the subject down-regulation is killing off the proliferating cells.

According to a third aspect the present invention relates to the use of PAI or functional derivative, equivalent, homologue, analogue or mimetic thereof, which PAI is bound, linked or otherwise associated with a toxin, in the manufacture of a medicament for the treatment of a condition in a mammal, which condition is characterized by the undesirable, detrimental or otherwise unwanted growth of cells expressing a uPA/uPAR complex. In a particularly preferred embodiment said PAI is PAI-2, while said toxin is an alpha-particle emitting radioisotope. Even more preferably said condition is a neoplasm, still more preferably a metastatic malignancy.

According to a fourth aspect the present invention relates to a PAI-2 conjugate molecule comprising PAI-2 or functional derivative, homologue, analogue, chemical equivalent or mimetic thereof, which PAI-2 is bound, linked or otherwise associated with a toxin or label.

Preferably the toxin or label is a radioisotope which can be detected with any means of radioactive detection, and more preferably is an alpha emitting radioisotope which includes, but is not limited to, Tb-149 or Bi-213.

Alternatively, the radioisotope is a gamma ray emitting particle which includes, but is not limited to, radioactive technetium (Tc-99m); or F-18 labeling, which is detected by Position Emission Tomography (PET).

According to a fifth aspect the present invention relates to a pharmaceutical composition comprising a PAI-2 conjugate molecule comprising PAI-2 or functional derivative, homologue, analogue, chemical equivalent or mimetic thereof, which PAI-2 is bound, linked or otherwise associated with a toxin or label in association with one or more pharmaceutically acceptable carriers and/or diluents. The pharmaceutical composition is preferably formulated for intravenous or subcutaneous application.

According to sixth aspect the present invention provides a method of detecting or visualizing cancerous cells, said method comprising contacting cells with a PAI-2 conjugate molecule comprising PAI-2 or functional derivative, homologue, analogue, chemical equivalent or mimetic thereof, which PAI-2 is bound, linked or otherwise associated with a label capable of being detected, and determining the cells that express a uPA/uPAR complex by detection or visualization.

Preferably the label is a radioisotope which can be detected by any means of radioactive detection, which radioisotope is preferably an alpha particle emitting radioisotope, a gamma ray emitting particle or a radioisotope which is detectable by Position Emission Tomography (PET).

The cells may be contacted with the PAI-2 conjugate molecule either in vitro or in vivo. In one embodiment the method is used to detect and visualize cancerous cells such as tumors and the location thereof in a mammalian body. The method may also be used to monitor changes in cancerous cells in the mammalian body to determine progression of cancer throughout the body, and to monitor the development of tumors, effectiveness of cancer treatment and therapy, and regression, remission or modulation of cancer in the body.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

DETAILED DESCRIPTION

Reference to "PAI" should be understood as a reference to any PAI or functional derivative, equivalent, homologue, analogue or mimetic thereof. In this regard, the PAI may be of any suitable form, such as a mature molecule, a precursor form of said mature molecule, mutant, polymorphic variant or a derivative, homologue, equivalent, analogue or mimetic thereof which exhibits at least one of the functional activities of said PAI. In a particularly preferred embodiment, said PAI is PAI-2, a glycoprotein of the serine protease inhibitor type and which exists in both glycosylated and unglycosylated forms. (Andreasen, 1990). Without limiting the present invention in any way, PAI-2 exhibits several advantages over PAI-1. First, PAI-2 is very stable in vitro compared to PAI-1 which is oxidation sensitive and easily inactivated (Kruithof et al., 1995). Secondly, PAI-2 is approximately 10,000 fold less active towards t-PA than PAI-1 and would not lead to the side effect that fibrinolysis is inhibited. Thirdly, high blood levels of PAI-2 are thought less likely to cause any other adverse side effects since high levels of PAI-2 are found during late pregnancy (in the non-pregnant state blood levels of PAI-2 are not detectable) and are not associated with toxicity (Kruithof et al., 1996).

Reference to "toxin" should be understood as a reference to any suitable toxin which achieves the object of providing a signal which reduces, prevents or otherwise inhibits the proliferation, differentiation or maintenance of subject cell (herein referred to as "down-regulating the growth" of said cell). The subject toxin may act by a variety of means including providing its signal via direct contact with a subject cell or emitting a molecule or particle, such as radiation in the case of a radioactive isotope toxin, which provides the signal to the subject cell. Preferably the toxin is a radioisotope and even more preferably a radioisotope which is highly toxic over a short range and exhibits a short half life thereby minimizing the occurrence of inadvertent toxicity on proximally located non-target cells. Most particularly, said radioisotope is an alpha particle emitting radioisotope. Examples of alpha-emitting radioisotopes suitable for use in the method of the present invention include, but are not limited to, Tb-149 or Bi-213. It should be understood that the toxin which is utilized in the method of the present invention may be in a purified, partially purified or unpurified form. It may also form a component of a larger molecule. The toxin may be naturally occurring or it may be synthetically or recombinantly produced.

Reference to "growth" of a cell should be understood as a reference to the proliferation, differentiation and/or maintenance of viability of the subject cell, while "down-regulating the growth" of a cell is a reference to reducing, preventing or inhibiting the proliferation, differentiation and/or maintenance of viability of the subject cell. In a preferred embodiment the subject growth is proliferation and the subject down-regulation is killing. In this regard, killing may be achieved either by delivering a fatal hit to the cell or by delivering to the cell a signal which induces the cell to apoptose.

Reference to "treatment" is to be considered in its broadest context. The term "treatment" does not necessarily imply that a mammal is treated until total recovery. Accordingly, "treatment" includes amelioration of the symptoms or severity of a particular condition or preventing or otherwise reducing the risk of developing a particular condition.

Reference to an "effective amount" means an amount necessary to at least partly attain the desired response.

It should be understood that the cell which is treated according to the method of the present invention may be treated in vitro or in vivo. A cell which is treated in vitro may be one that has been removed from the body of a mammal. For example, cells or tissue comprising neoplastic cells may be removed from a mammal, treated according to the method of the present invention to down-regulate or induce apoptosis of the neoplastic cells and then returned to the mammal. Alternatively, the in vitro cell may be a cell line in respect of which it is sought to down-regulate or modulate its apoptic behavior via the methods disclosed herein. In accordance with the preferred aspect of the present invention, the cell may be a neoplastic cell (such as a malignant cell) located in vivo and the induction of apoptosis would be achieved by applying the method of the present invention in vivo. It should be understood that where reference is made to a specific cell type which is located in vivo, such as a breast cancer cell, prostate cancer cell or colorectal cancer cell, this cell may be located at the expected site in the mammal or, if a primary cancer has metastasized, the subject cancer may be located in another region of the patient's body. For example, it may form part of a secondary tumor (metastasis) which is located, for example, in the liver, lymph node or bone.

The present invention is directed to inhibiting the unwanted growth of cells expressing a uPA/uPAR complex. This should be understood as a reference to cells expressing uPAR (the uPA receptor) to which is coupled a uPA molecule.

The uPA molecule which has bound to the uPAR may be derived from any source and has not necessarily been produced from the subject cell in an autocrine fashion—although it should be understood that this possibility is not excluded. Without limiting the present invention to any one theory or mode of action, PAI-2 (to which has been coupled a toxin) will interact with the uPA molecule which, in turn, has interacted with the uPAR expressed by the subject cell. The PAI-2 is thereby specifically targeted to cells which express a uPAR to which is bound uPA. Still without limiting the present invention in any way, uPAR is expressed by neoplastic cells and is not expressed at significant levels by non-neoplastic cells.

Reference to "interact" should be understood as a reference to any form of interaction. Said interaction may occur via the formation of bonds such as covalent bonds, hydrogen bonds, van Der Waals forces or via any other mechanism of interaction.

Reference to "neoplastic cell" should be understood, in the context of the present invention, as a reference to a cell exhibiting abnormal growth (as hereinbefore defined) and which cell expresses uPAR. The neoplastic cell may be a benign cell or a malignant cell. Preferably, the cell is malignant. Without limiting the present invention in any way, uPAR is overexpressed in metastatic cancers including, but not limited to, breast cancer, prostate cancer and colorectal cancer.

"Functional derivatives and mimetics" include fragments, parts, portions, mutants, and mimetics from natural, synthetic or recombinant sources including fusion proteins exhibiting any one or more of the functional activities of the subject PAI or toxin. To the extent that the subject PAI or toxin is a protein, derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences including fusions with other peptides, polypeptides or proteins.

Homologues of a PAI or toxin contemplated herein include, but are not limited to, molecules derived from different species.

Chemical and functional equivalents of PAI or toxin should be understood as molecules exhibiting any one or more of the functional activities of PAI or toxin, respectively, and may be derived from any source such as being chemically synthesized or identified via screening processes such as natural product screening.

The derivatives of PAI or toxin include fragments having particular epitopes of parts of the entire PAI protein or toxin fused to peptides, polypeptides or other proteinaceous or non-proteinaceous molecules. For example, PAI or derivative thereof may be fused to a molecule to facilitate its delivery to a cell.

"Analogues" of PAI or toxin contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 1.

TABLE 1

| Non-conventional amino acid | Code |
| --- | --- |
| -aminobutyric acid | Abu |
| -amino-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |

TABLE 1-continued

| Non-conventional amino acid | Code |
| --- | --- |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-methylalanine | Dmala |
| D-methylarginine | Dmarg |
| D-methylasparagine | Dmasn |
| D-methylaspartate | Dmasp |
| D-methylcysteine | Dmcys |
| D-methylglutamine | Dmgln |
| D-methylhistidine | Dmhis |
| D-methylisoleucine | Dmile |
| D-methylleucine | Dmleu |
| D-methyllysine | Dmlys |
| D-methylmethionine | Dmmet |
| D-methylornithine | Dmorn |
| D-methylphenylalanine | Dmphe |
| D-methylproline | Dmpro |
| D-methylserine | Dmser |
| D-methylthreonine | Dmthr |
| D-methyltryptophan | Dmtrp |
| D-methyltyrosine | Dmty |
| D-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| -aminobutyric acid | Gabu |
| L-t-butylglycine | Tbug |
| L-ethylglycine | Etg |
| L-homophenylalanine | Hphe |
| L-methylarginine | Marg |
| L-methylaspartate | Masp |
| L-methylcysteine | Mcys |
| L-methylglutamine | Mgln |
| L-methylhistidine | Mhis |
| L-methylisoleucine | Mile |
| L-methylleucine | Mleu |
| L-methylmethionine | Mmet |
| L-methylnorvaline | Mnva |
| L-methylphenylalanine | Mphe |
| L-methylserine | Mser |
| L-methyltryptophan | Mtrp |
| L-methylvaline | Mval |
| N-(N-(2,2-diphenylethyl) carbamylmethyl)glycine | Nnbhm |
| 1-carboxy-1-(2,2-diphenyl- L-N-methylalanine | Nmbc Nmala |

TABLE 1-continued

| Non-conventional amino acid | Code |
|---|---|
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| -methyl-aminoisobutyrate | Maib |
| -methyl-aminobutyrate | Mgabu |
| -methylcyclohexylalanine | Mchexa |
| -methylcylcopentylalanine | Mcpen |
| -methyl-napthylalanine | Manap |
| -methylpenicillamine | Mpen |
| N-(4-aminobutyl)glycine | Nglu |
| N-(2-aminoethyl)glycine | Naeg |
| N-(3-aminopropyl)glycine | Norn |
| N-amino-methylbutyrate | Nmaabu |
| -napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-methylalanine | Mala |
| L-methylasparagine | Masn |
| L-methyl-t-butylglycine | Mtbug |
| L-methylethylglycine | Metg |
| L-methylglutamate | Mglu |
| L-methylhomophenylalanine | Mhphe |
| N-(2-methylthioethyl)glycine | Nmet |

TABLE 1-continued

| Non-conventional amino acid | Code |
|---|---|
| L-methyllysine | Mlys |
| L-methylnorleucine | Mnle |
| L-methylornithine | Morn |
| L-methylproline | Mpro |
| L-methylthreonine | Mthr |
| L-methyltyrosine | Mtyr |
| L-N-methylhomophenylalanine | Nmhphe |
| N-(N-(3,3-diphenylpropyl) carbamylmethyl)glycine ethylamino)cyclopropane | Nnbhe |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

Without limiting the present invention to any one theory or mode of action, it is thought that PAI-2 exhibits high selectivity to neoplastic cells at their most malignant phase. In this regard, PAI-2 functions as a "homing molecule" for cancer cells which express uPA, bound to uPA receptors, on their surface. Upon binding of radiolabelled PAI-2 to the cell surface uPA/uPAR complex, the entire molecular complex is internalized. Once internalized, the high energy radioactive emission kills the subject cell with little or no effect on proximally located non-target cells. Due to the absence of such side effects, together with the short half-life and rapid decay of the selected alpha particle emitting radioisotope, there is little or no detrimental effect to the subject as a whole. The high turnover cell toxicity of radiolabelled PAI-2 is thought to derive from the tight, essentially irreversible binding of PA-2 to uPA.

Still without limiting the present invention in any way, Tb-149 and Bi-213, in particular, chelate to PAI-2 to form very stable bonding. In this regard, any suitable method may be utilized to achieve chelation. Preferably, the chelators cDTPA and CHX-A are utilized. Alpha radiation can then kill the subject cancer cells in 1-5 nuclear hits. This linear energy transfer (LET) for the particle, being very much greater than that for the beta rays, causes a high relative biological effectiveness over a much shorter range. As a result, a much greater fraction of the total energy is deposited in cells with alphas and very few nuclear hits are required to kill a cell (Lloyd et al., 1979, Kassis et al., 1986). Further, the short half life of alpha-emitters is particularly suitable for the killing of cancer cells and pre-angiogenic lesions while simultaneously releasing only a low radiation dose to normal tissue. The alpha therapeutic ratio is thought to be two orders of magnitude greater than that for a high energy beta emitter and is therefore the preferred form of toxin for use in the method of the present invention.

Administration of the toxin labeled PAI, in the form of a pharmaceutical composition, may be performed by any convenient means. The toxin labeled PAI of the pharmaceutical composition are contemplated to exhibit therapeutic activity when administered in an amount which depends on the particular case. The variation depends, for example, on the human or animal and the toxin chosen. A broad range of doses may be applicable. Considering a patient, for example, from about 0.1 µg to about 10 mg of toxin labeled PAI may be administered per kilogram of body weight per day. For example from about 0.1 µg-5 mg, 10 µg-5 mg or 100 µg-1 mg. Dosage regimes may be adjusted to provide the optimum therapeutic response. For example, several divided doses may be administered daily, weekly, monthly or other suitable time intervals or the dose may be proportionally reduced as indicated by the exigencies of the situation. The toxin labeled PAI may be administered in any convenient manner such as by the intravenous, intraperitoneal, intramuscular, subcutaneous or intradermal. Preferably, the toxin-labeled PAI is administered intravenously or subcutaneously.

In accordance with these methods, the toxin labeled PAI defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules, These molecules may be administered in any order.

The term "mammal" should be understood as a reference to a human, primate, livestock animal (eg. sheep, pig, cow, horse, donkey) laboratory test animal (eg. mouse, rat, rabbit, guinea pig) companion animal (eg. dog, cat) or captive wild animal (eg. fox, kangaroo, deer). Preferably, the mammal is a human.

The pharmaceutical forms of the PAI-2 conjugate molecule of the present invention suitable for injectable use include sterile aqueous solutions (where water soluble) and sterile powders for the extemporaneous preparation of sterile injectable solutions or dispersion. In all cases the form must be sterile and must be fluid to the extent that easy syringability exists. It must be stable under the conditions of manufacture and storage and may be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimersal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.1 µg to about 2000 mg. Expressed in proportions, the active compound is generally present in from about 0.1 µg to about 2000 mg/ml of carrier. In the case of compositions containing supplementary active ingredients, the dosages are determined by reference to the usual dose and manner of administration of the said ingredients.

The present invention is further described by the following non-limiting Examples and accompanying drawings.

EXAMPLE 1

Preparation of PAI-2 Alpha-Emitter Conjugate

Production

Figure 1:
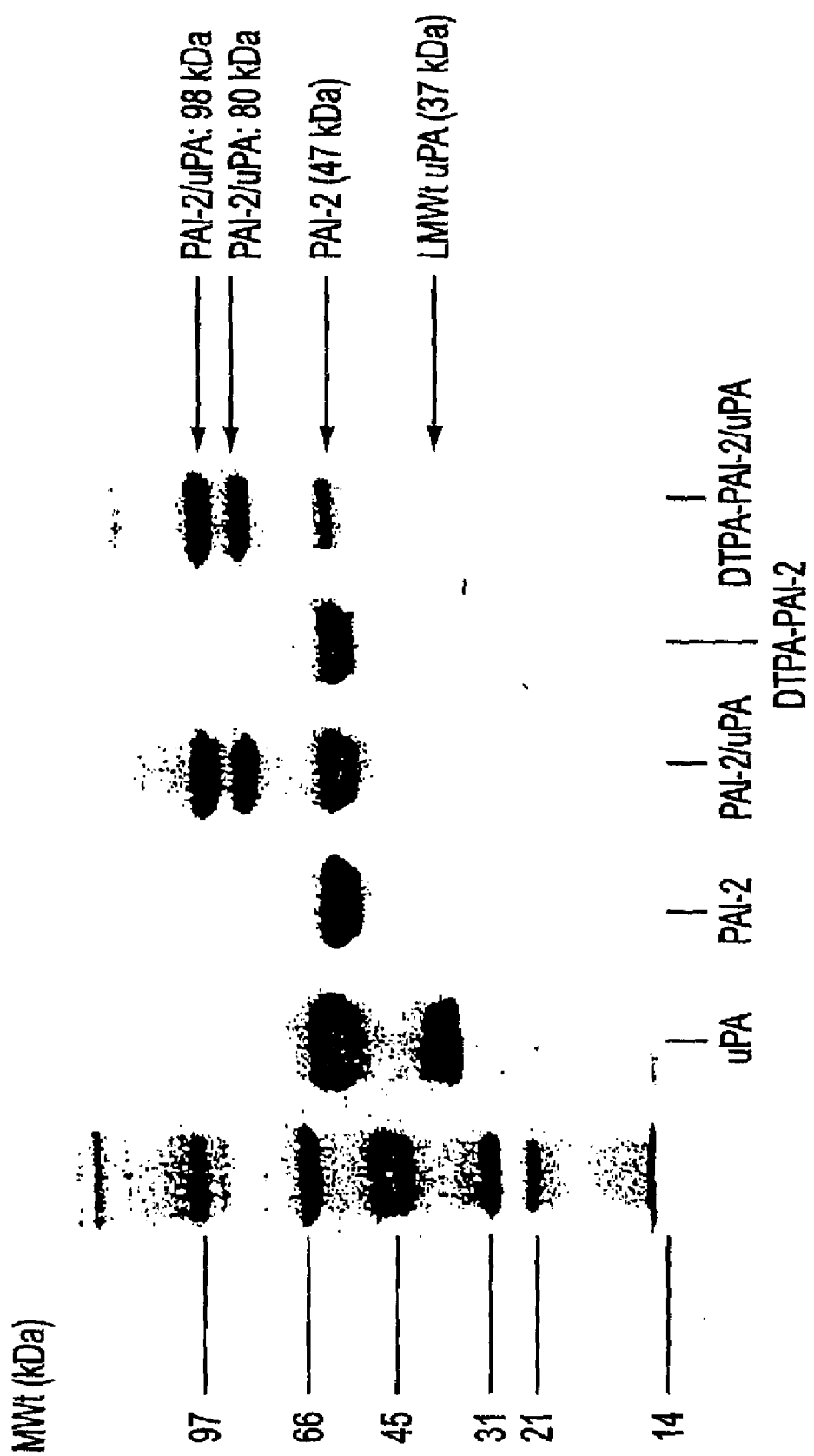
FIG. 1 Formation of SDS-stable complex of radio-conjugated PAI-2 with uPA, indicating activity of PAI-2.

The rare earth nuclide $^{149}$Tb is produced on a tandem, cyclotron or linear accelerator using high energy heavy ions such as boron or carbon or nitrogen ions to bombard targets of Praseodymium, eg. Pr($^{12}$C,4n) or Neodymium Nd($^{12}$C,5n) at higher energies. Metal targets are rolled and mounted on a frame. A thin target has 1 mg cm$^{-2}$, a thick target has 30 mg cm$^{-2}$. A catcher foil is used to collect Tb ions in the thin foil geometry.

Tb-149 is also produced via the spallation reaction of high energy charged particles, eg. protons, on a high atomic number target such as tantalum. The ions are passed through a magnetic mass analyzer to select the A=149 component of the yield. The Tb-immunoconjugates are made using the longer lived isotope Tb-152 as an exact analogue.

An alternative radiolabel is Bi-213, which is produced by decay from Ac-225. the Bi-213 is eluted from the Ac-225 with 250 µL of fresh 0.15 M HI followed by 250 µL water. The activity of the Bi-213 is assayed against the Au-198 setting in the dose calibrator. The first elution is not used as it contains cold Bi.

Purification

In the production of Tb-149, the product nuclides are separated from the thick target by dissolution in 6 M nitric acid, the sample is irradiated to dryness and yield determined by gamma ray spectroscopy. The residue is dissolved in 0.16 M—hydroxyisobutyric acid and passed through a cation exchange column (particle size 13 µm). The pH of the eluant is adjusted to 5 by aqueous ammonia. Elution was under a pressure of 7 kg cm$^{-2}$ at a flow rate of 0.5 mL min$^{-1}$. Terbium fractions are dried gently and heated to 450 degrees to destroy the Tb-isobutyrate complex. The residue is dissolved in dilute nitric or hydrochloric acid for the radiolabeling procedure.

Bi-213 is eluted with 0.15 M hydriodic acid and the pH of the eluant adjusted as above.

Labeling

The purified product is chelated to molecules which target specific cancer cells. A number of different chelation procedures are available in the literature which use cDTPA, CHX-A, DTPA-CHX, DOTA (1,4,7,10-tetraazacyclododecane-N,N,N,N,tetraacetic acid), and TETA.

The labeling procedure is a modification of the method used by Izard et al (1992). Briefly, both chelators, i.e., cDTPA and CHX-A, were prepared in chloroform and were purified under a stream of Nitrogen. A chelator:protein molar ratio of 20:1 and 4:1 was maintained for cDTPA and CHX-A respectively. After a 45-minute on-ice incubation of the chelator and PAI-2 (Biotech Australia), the conjugate was purified on a PD-10 column (Pharmacia Biotech) using 0.5 M sodium acetate at pH 5.5 as the eluting buffer. This was followed by the addition of Bi-213 and Tb-149 or Tb-152. After 20-minute incubation, the ratio-conjugate (RI) was again purified on another PD-10 column using PBS at pH 7.0 as the eluting buffer. The protein recovery is >97% as determined by instant thin layer chromatography (ITLC) of the fractions obtained. A similar procedure was followed for labeling the non-specific protein, bovine serum albumin (BSA).

The inhibitory activity of cDTPA-conjugated PAI-2 was confirmed by its ability to form complexes after 40 min incubation at 20° C. with active uPA. Complex formation was detected by a molecular mass shift by SDS-PAGE (12% non-reducing gel) (FIG. 1).

Stability of Radioconjugated Protein

Figure 2:
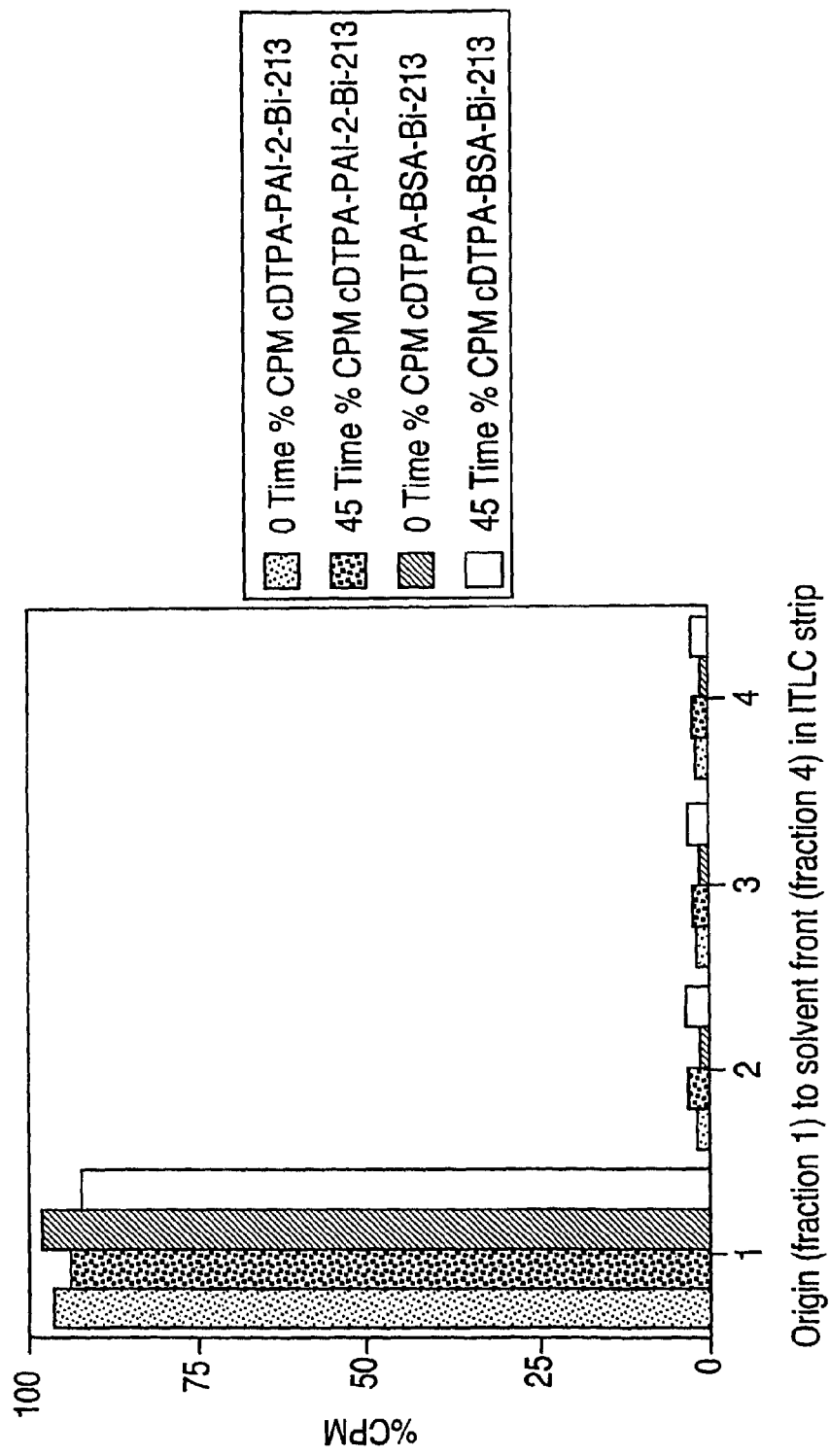
FIG. 2 Purity of radio-conjugated PAI-2 in ITLC.

The radioconjugates were incubated with fresh human serum at 37° C. for 45 min (equivalent to one half-life for Bi-213). Samples were then analyzed by ITLC (FIG. 2). Radioconjugates remain at the origin whereas any free label runs at the solvent front. Similar experiments have been performed with Tb radioconjugates over long time periods.

EXAMPLE 2

In Vitro Analysis of PAI-2 Alpha Emitter Conjugate

Tb-149 and Bi-213 labeled protein conjugates have been produced and their stability, labeling efficiency, targeting and in vitro cell survival (37% survival for 2 µCi) with MDA-MB-231 and MCF-7 breast cancer cell lines have been tested. The following Tb-149 and Bi-213 labeled protein conjugates have been prepared, by the inventors, for the first time:

Tb-149.cDTPA.PAI-2
Tb-149.CHX.PAI-2
Bi-213.cDTPA.PAI-2
Bi-213.CHX.PAI-2

The method of the present invention is suitable for any early stage metastatic cancer which express high levels of uPA-uPAR.

Cell Survival

Cell survival data have been obtained for two cell lines (MDA-MB-231 and MCF-7) in the presence of plasminogen with or without the specific uPA activity blocking agent {gly-gly-arg chloromethylketone (EGR-CMK), as this agent effectively inhibits PAI2 binding; Hang et al. 1998}. The 37% survival dose ($D_o$) values are shown in Table 2.

TABLE 2

Percentage cell survival at 5 µCi activity of alpha-proteins or at excess concentrations of cDTPA-PAI-2 and PAI-2 compared to controls.

| Cells | Alpha-PAI-2[1,2,4] | | Alpha-BSA[1,3] | | cDTPA-PAI-2[3] (37.5 µg/mL) | PAI-2[3] (50 µg/mL) |
|---|---|---|---|---|---|---|
| | − | + | − | + | | |
| MDA-MB-231 | 11.2 ± 2.9 | 39.8 ± 4.3 | 87.5 ± 5.4 | 87.3 ± 5.1 | 97.5 ± 2.1 | 98.0 ± 1.4 |
| MCF-7 | 12.8 ± 2.6 | 39.5 ± 3.3 | 86.7 ± 4.8 | 85.8 ± 5.2 | 97.5 ± 1.3 | 97.5 ± 2.2 |
| Leukocytes | 98.0 ± 2.8 | 93.5 ± 6.4 | ND | | ND | ND |

[1] − and + indicate without and with EGR-CMK pre-treatment. ND = not determined.
[2] Values shown are the means ± DK (n = 6, each experiment performed in triplicate)
[3] Values shown are the means ± SK (n = 2, each experiment performed in triplicate).
[4] Protein concentration of alpha-PAI-2 was approximately 2.5 µg/mL.

Figure 3:
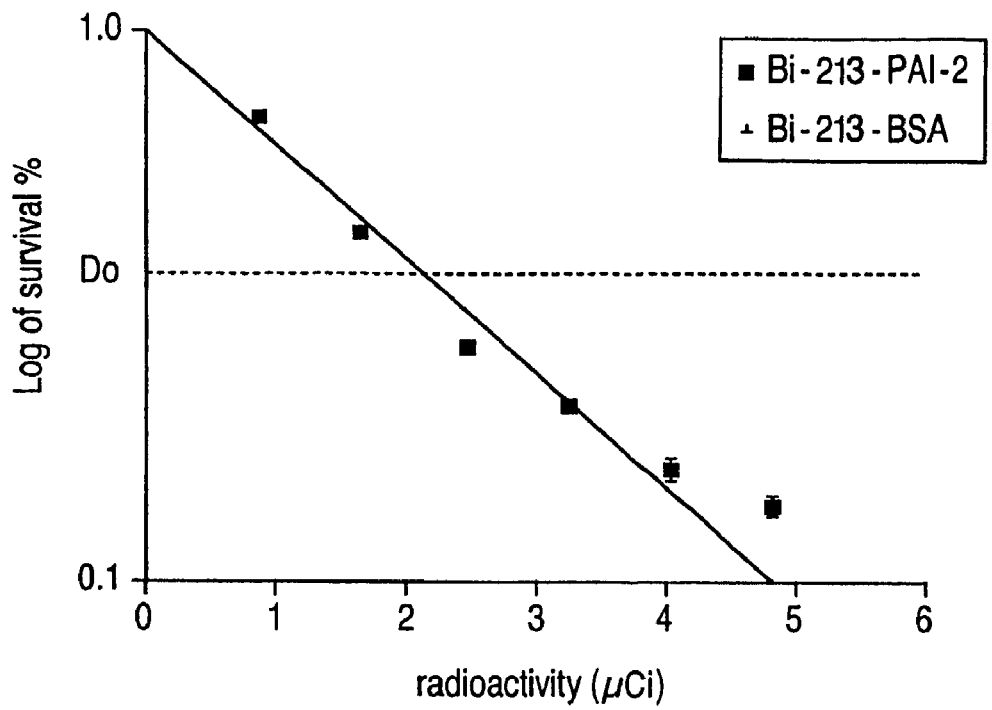
FIG. 3 MDA-MB-231 cell survival with radio-conjugate PAI-2.
Figure 4:
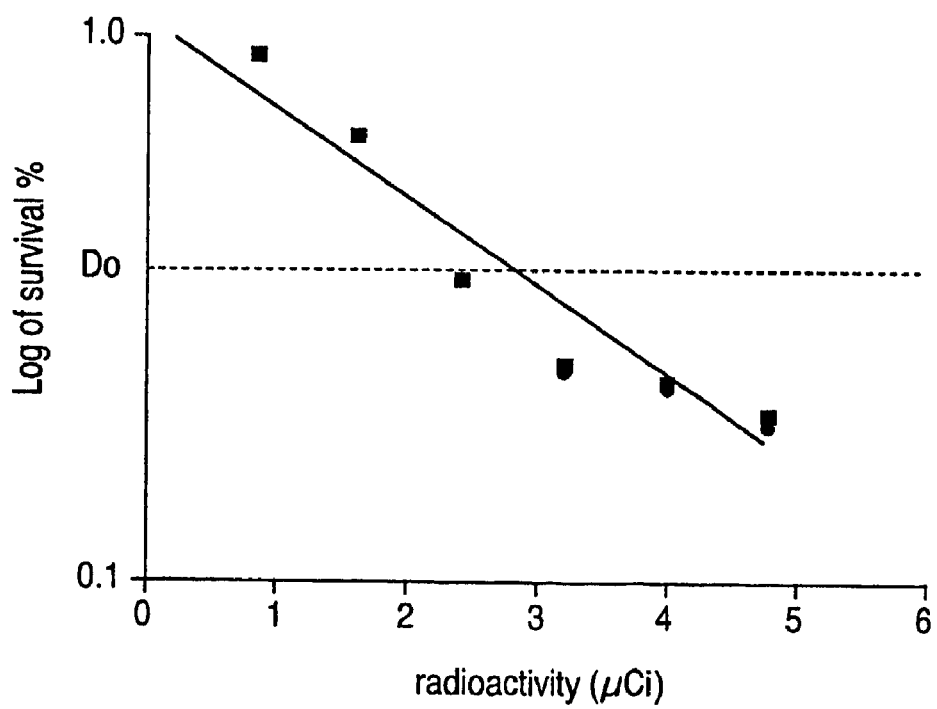
FIG. 4 MCF-7 cell survival with radio-conjugate PAI-2.

Conclusions:

a) EGR-CMK significantly improves survival (by a factor of 2.5, Table 2) as a result of inhibition of the PAI-2 interaction with cellular uPA, proving the specific cytotoxicity of Bi-213.cDTPA.PAI-2.

b) MDA-MB-231 and MCF-7 have similar survivals (i.e. about 2 µCi for 37%), as shown in FIGS. 3 and 4. This does not imply similar cellular uPA levels but rather the high toxicity of the Bi-213.cDTPA.PAI-2.

c) No cell killing was observed with the freshly isolated normal human leukocytes (Table 2) reflecting that non-targeted cells are immune from Bi-213.cDTPA.PAI-2.

Endocytosis

Figure 5A:
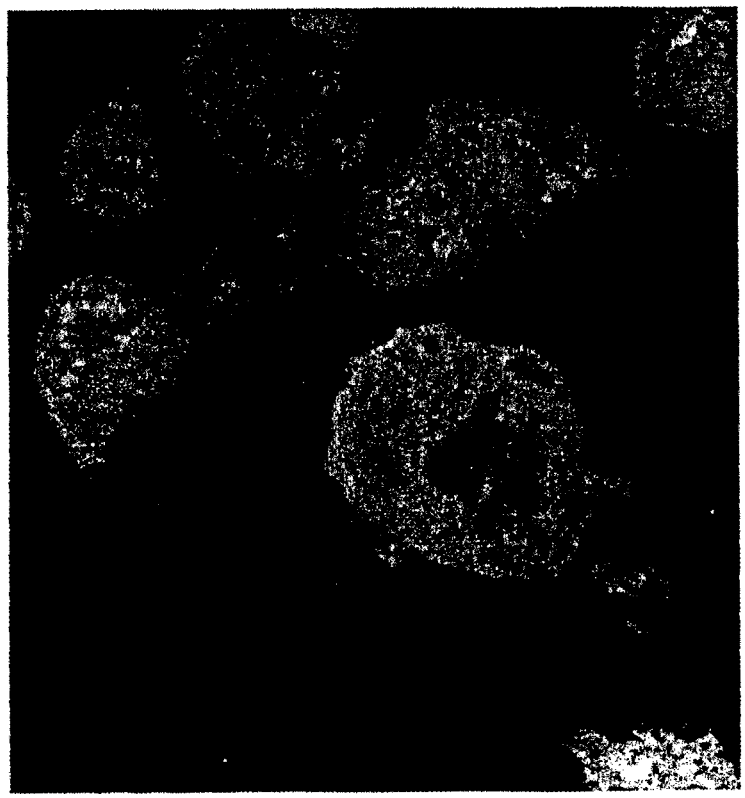
FIGS. 5A-B Confocal microscopy of endocytosis of radio-conjugate PAI-2 by MDA-MB-231 cells.
Figure 5B:
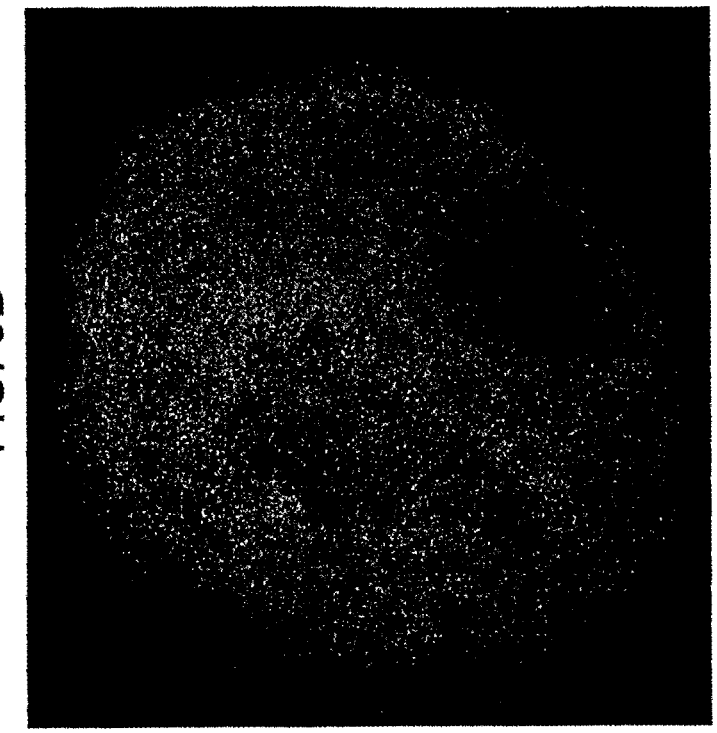

The Bi-213.cDTPA.PAI-2:uPA complex is endocytosed in breast cancer cells, as shown by confocal microscopy in FIGS. 5A-B. Some cells shown in FIGS. 5A-B have been stably transfected with the green fluorescent protein (GFP). This uncloned population was then incubated with TRITC— (red fluorescene) labeled PAI-2 (10 µg/ml) for 1 h at room temperature before being viewed under the confocal microscope. The red fluorescent spots are evidence of internalization and accumulation into vesicles (probably endosomes and lysosomes). Internalization improves the cytotoxicity for isolated cells as the probability for alpha tracks crossing the nucleus is increased.

EXAMPLE 3

Tolerance of Alpha-PAI-2 in Mice

Alpha-PAI-2 was administered by intra-peritoneal injection in adult (10-12 weeks), male BALB/c nude mice at a dose of 3 mCi/kg (i.e. 3 times the accepted tolerance dose in humans for an alpha-labelled antibody; D. Scheinberg, Memorial Sloan Kettering Institute, personal communication to B. Allen). A 10% short-term weight loss was observed in 2 of 3 mice with recovery by day 11. The third mouse lost approximately 10% body weight at day 7 and was stable at this level. Cold chelated-PAI-2 (DTTAPAI-2), cold PAI-2 and the control (saline) mouse all showed small variations in weight.

Figure 6:
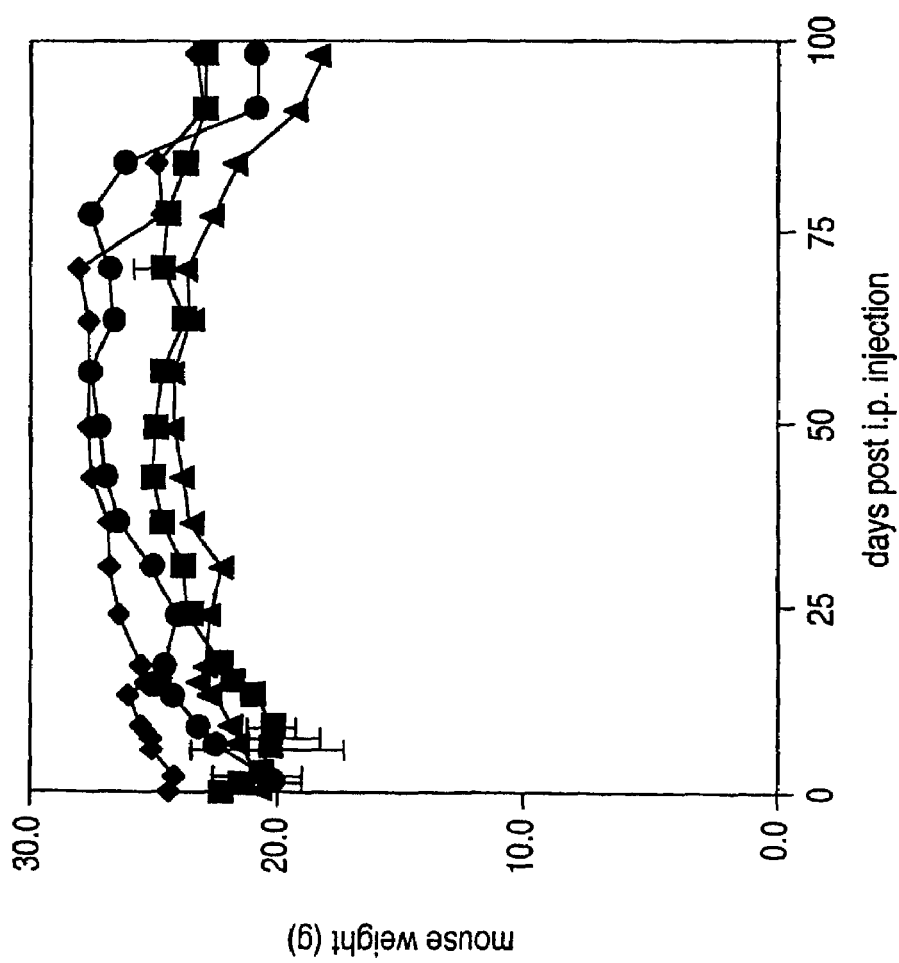
FIG. 6 Alpha-PAI-2 tolerance study in nude mice (3 mCi/kg).

These mice were monitored for 100 days and the mouse weights are shown in FIG. 6.

Overall, the mice were clinically unaffected for the time period observed.

Figure 7:
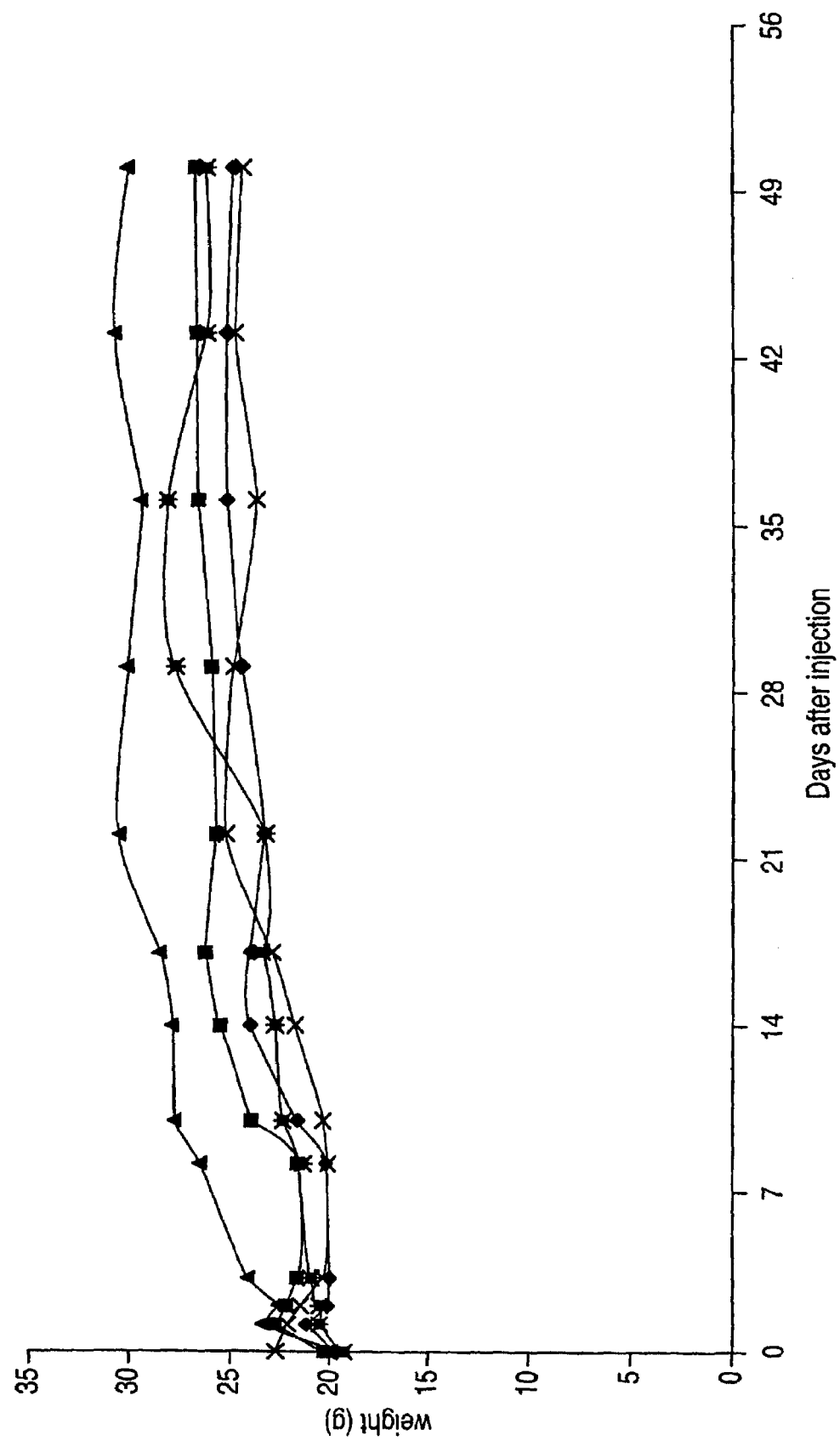
FIG. 7 Alpha-PAI-2 tolerance study in nude mice (6 mCi/kg, i.v. injection).
Figure 8:
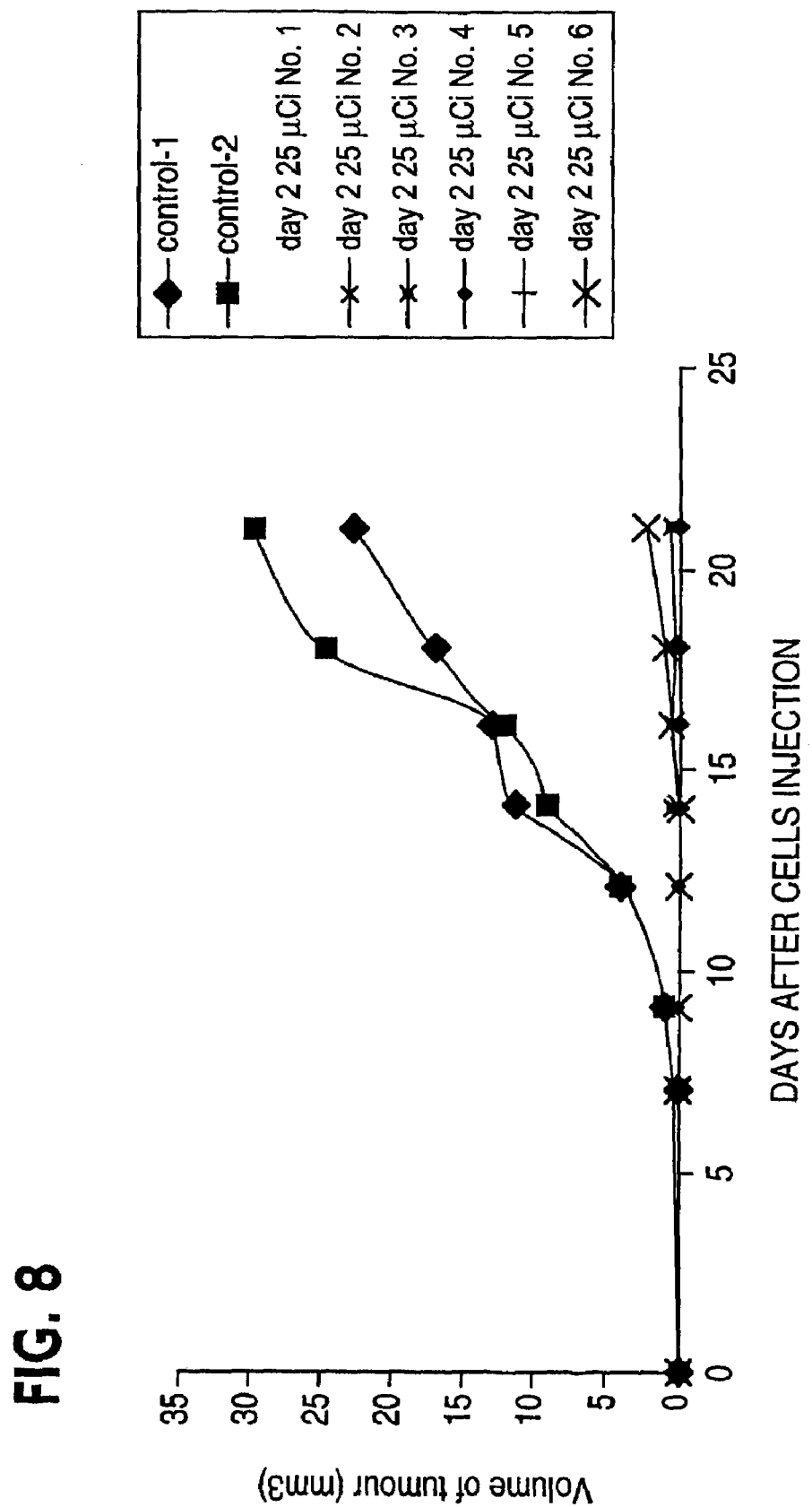
FIG. 8 Breast Cancer in vivo model. 25 µCi radio-conjugate PAI-2 injected 2 days after tumor cells.
Figure 9:
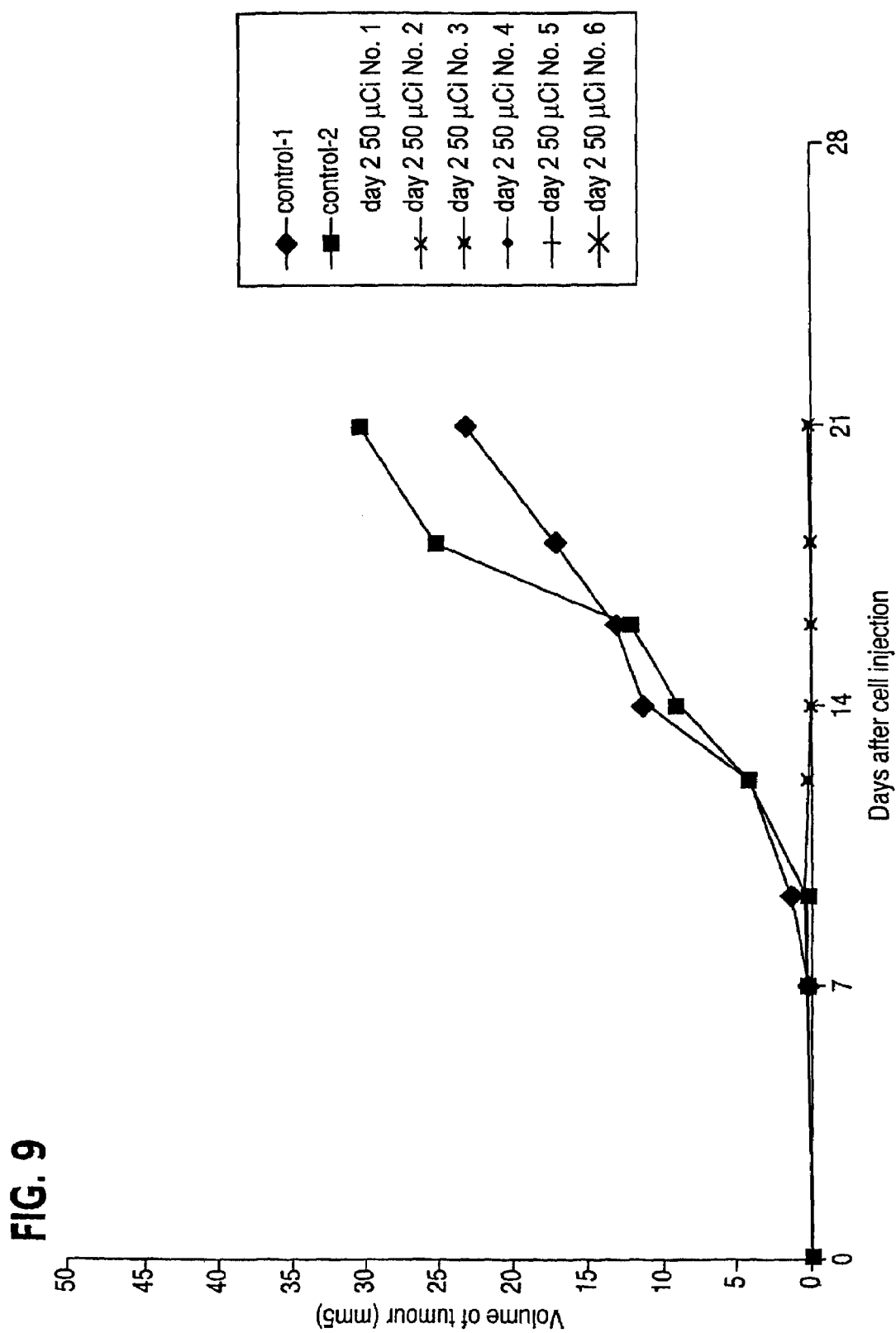
FIG. 9 Breast Cancer in vivo model. 50 µCi radio-conjugate PAI-2 injected 2 days after tumor cells.
Figure 10:
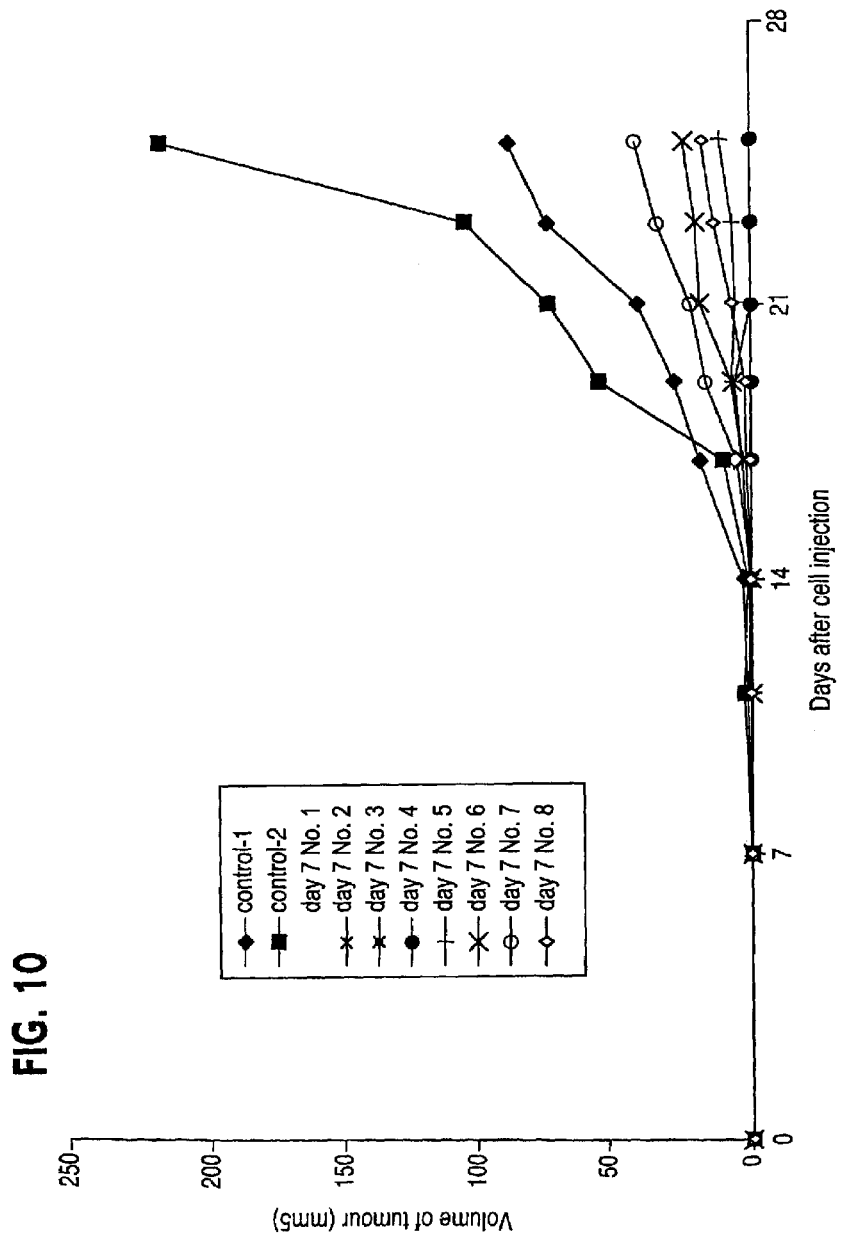
FIG. 10 Breast Cancer in vivo model. 25 µCi radio-conjugate PAI-2 injected 7 days after tumor cells.
Figure 11:
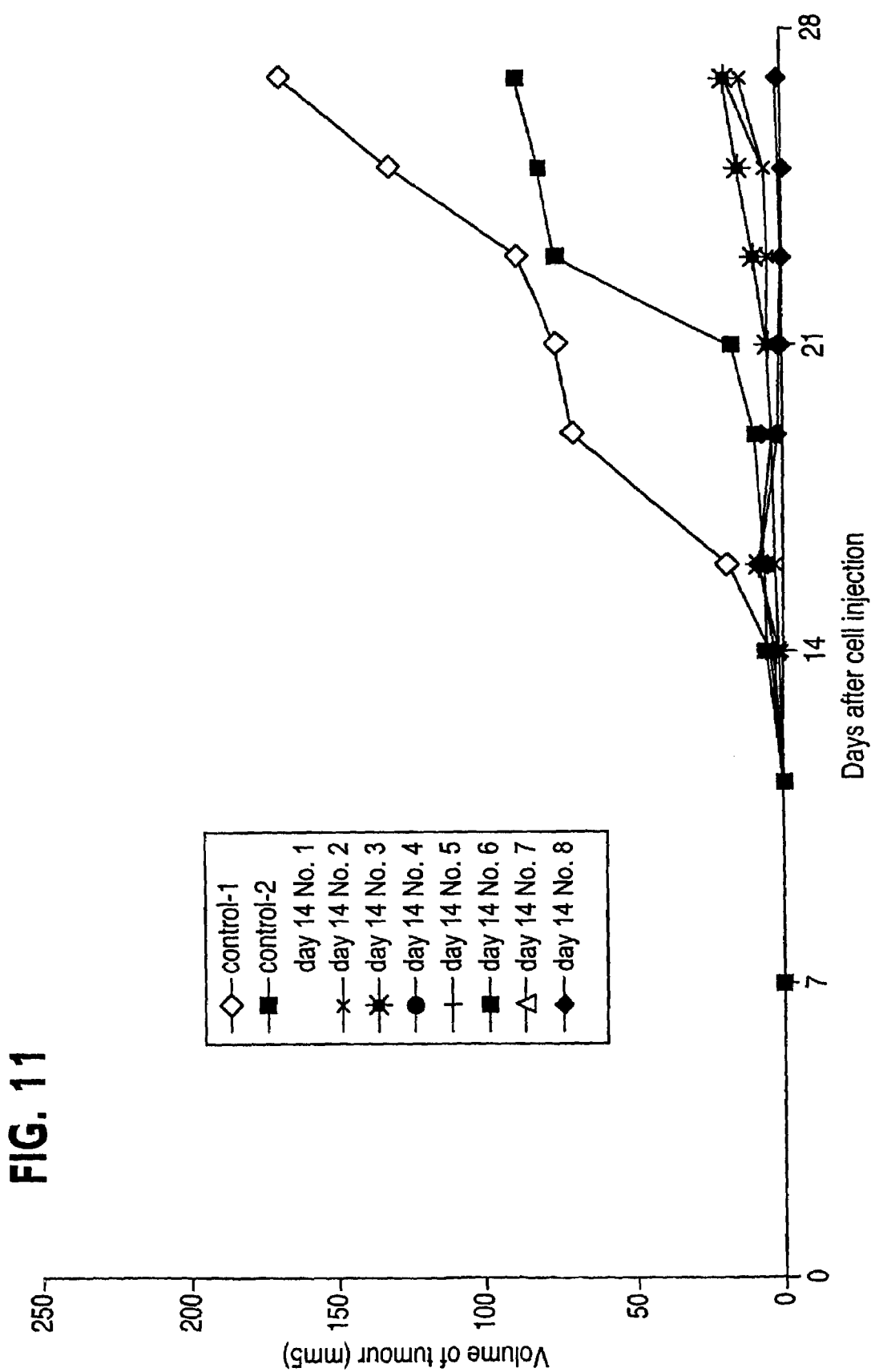
FIG. 11 Breast cancer in vivo model. 25 µCi radio-conjugate PAI-2 injected 14 days after tumor cells.
Figure 12A:
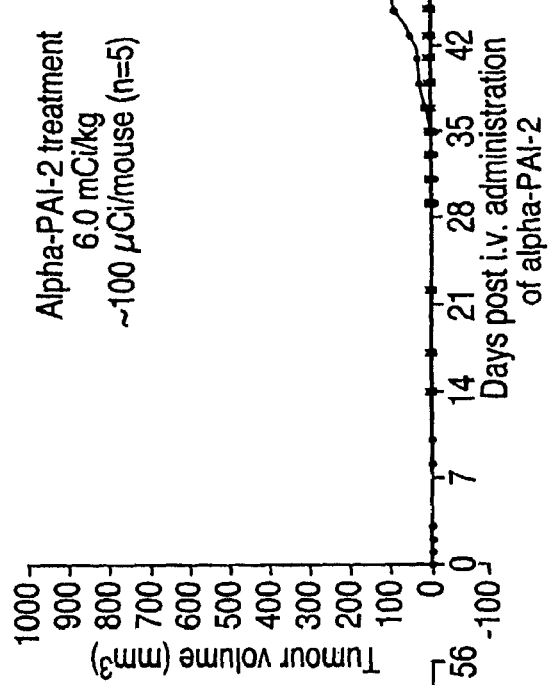
FIGS. 12A-D Alpha-PAI-2 or non-specific alpha-protein administered 2 days post inoculation of human breast cancer MDA-MB-231 cells in nude mice.
Figure 12B:
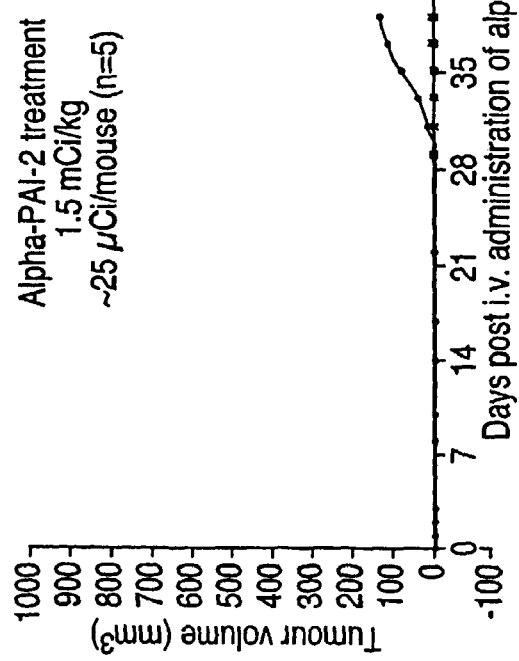
Figure 12D:
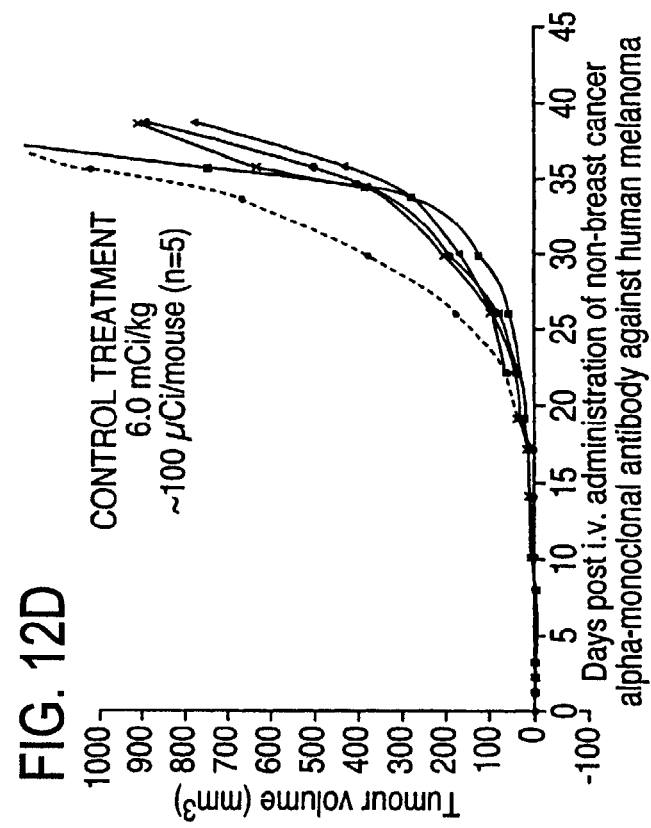
Figure 12C:
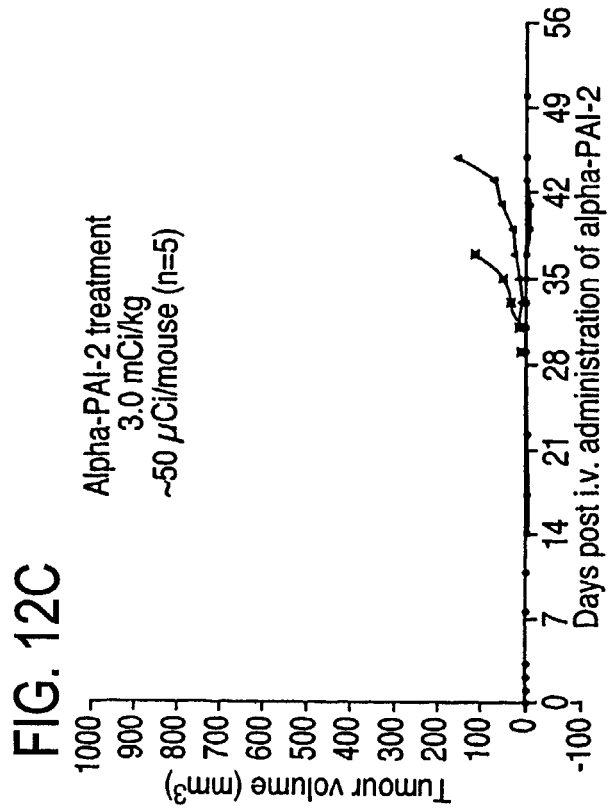

To investigate the tolerance of mice to intravenous administration of the drug, alpha-PAI-2 (6 mCi/kg) was administered by tail vein injection in 8-10 week old female Arc(s) nude mice (FIG. 7). There were five mice (noted n=5) per dose. Weight changes were minimal (less than % 10) within the first 7 days, in most mice no change was noted. Similar results were obtained using a non-specific monoclonal antibody. All mice gained weight to adult levels and remained stable over the study period shown.

These experiments demonstrate that alpha-PAI-2 is well tolerated in these animals, to a dose of 6 mCi/kg.

EXAMPLE 4

Breast Cancer Model

Two million human breast cancer cells [MDA-MB-231 (mycoplasma free)] in sterile phosphate buffered saline (PBS) were injected sub-cutaneously into the mammary fat pad of first pair breasts on both sides of 4-6 week old female nude mice.

At 2, 7 and 14 days post cell innoculation, each mouse was injected s.c. at the site of tumor cell inoculation with either PBS (control) or varying doses of—alpha-PAI-2 in PBS (described as Bi-213.cDPTA.PAI-2 in figures; specific activity 3-4 µCi/10 µL). The maximum volume injected at any one time was 100-120 µl/site. Note that all mice were handled similarly and kept under similar feeding and housing conditions. The results are shown in FIGS. 8, 9, 10 and 11.

The tumor volume was recorded for each mouse at various time points since inoculation of breast cancer cells (indicated on x-axis of figures as days after cell injection). The skin in area of inoculation was monitored for any signs of inflammation or damage—none were recorded. Also weight and overall well-being was monitored from time of cell innoculation. These were all normal except for a small decrease in weight (~10%) immediately after alpha-PAI-2 which was quickly recovered (data not shown). A similar phenomenon was seen with alpha-PAI-2 treatment of mice without tumors in the alpha-PAI-2 tolerance study (FIG. 6 from Example 3).

The mice are monitored for another 2-3 weeks after which they are sacrificed for the purpose of performing histological analysis of tissues associated with the injection site, including auxiliary lymph node tissue for the presence of cancer cells.

FIGS. 8, 9, 10 and 11 show that significant reduction in tumor volume occurred with injection of radio-conjugate PAI-2. This was apparent with two doses of PAI-2, 25 µCi (FIG. 8) or 50 µCi (FIG. 9) injected 2 days after the inoculation of cancer cells into the mammary fat pad of the mouse. It was also apparent when the radio-conjugate PAI-2 was injected 7 days (FIG. 10) or 14 days (FIG. 11) after the tumor cells.

EXAMPLE 5

Intravenous Targeted Alpha Therapy (TAT) with Alpha-PAI-2 in Breast Cancer Xenografted Nude Mice A further study was carried out with intravenous administration of the drug.

Two million human breast cancer cells [MDA-MB-231 (mycoplasma free)] in sterile phosphate buffered saline (PBS) were injected sub-cutaneously into the mammary fat pad of first pair breasts on both sides of 4-6 week old female nude mice. At 2 days post-cell inoculation, each mouse was administered either alpha-PAI-2 (1.5 mCi/kg, 3 mCi/kg or 6 mCi/kg) or non-specific alpha-MAb (6 mCi/kg) by tail vein injection. There were five mice (noted n=5) per dose. The maximum volume injected at any one time was 100-120 µl/site. Note that all mice were handled similarly and kept under similar feeding and housing conditions.

The tumor volume was recorded for each mouse at various time points since inoculation of breast cancer cells (indicated on x-axis of figures as days after administration). The skin in the area of inoculation was monitored for any signs of inflammation or damage—none was recorded. Also weight and overall well-being was monitored from time of cell inoculation. There was no change except for a small decrease in weight (~10%) imediately after alpha-PAI-2 treatment in some mice which was quickly recovered (data not shown).

The results are presented in FIGS. 12A-D, and clearly show that alpha-PAI-2 (Bi-213.cDTPA.PAI-2) administered intravenously can inhibit tumor growth. There is also a dosage effect—6 mCi/kg being more effective than 3 mCi/kg, which was more effective than 1.5 mCi/kg.

The mice were sacrificed at the last time point for tumor size measurements for the purpose of performing histological analysis of tissues associated with the cell inoculation site, as well as axillary lymph node tissue for the presence of cancer cells. By macroscopic inspection axillary lymph nodes appeared unaffected compared to non-specific protein control mice that had enlarged and hardened lymph nodes.

EXAMPLE 6

Alpha-PAI-2 Inhibition of Prostate Cancer

For the investigation of prostate cancer, cells from the human prostate adenocarcinoma, PC-3, were harvested and washed in culture medium. Then $2 \times 10^6$ cells were resuspended in 100 µL of the RPMI-1640 serum-free medium and 100 gL of matrigel (Becton Dickinson, Bedford Mass.) and injected via 18-gauge needle into the s.c. space of the right flank region of male 6-8 week old athymic nude mice, BALB/c (nu/nu). Because PC-3 cells require additional factors or stromal cells, it is necessary to co-inject the cells with matrigel to induce tumor growth in nude mice.

Figure 14:
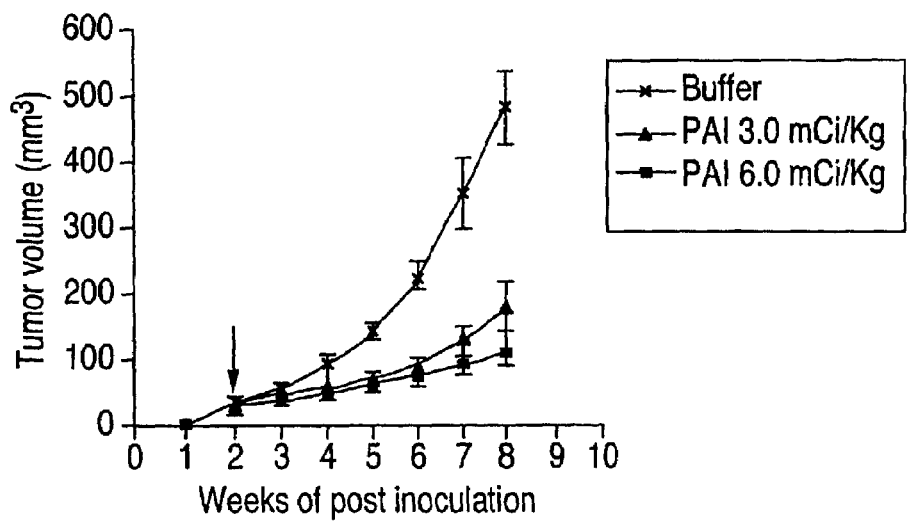
FIG. 14 Systemic TAT post tumor appearance in first week.
Figure 15:
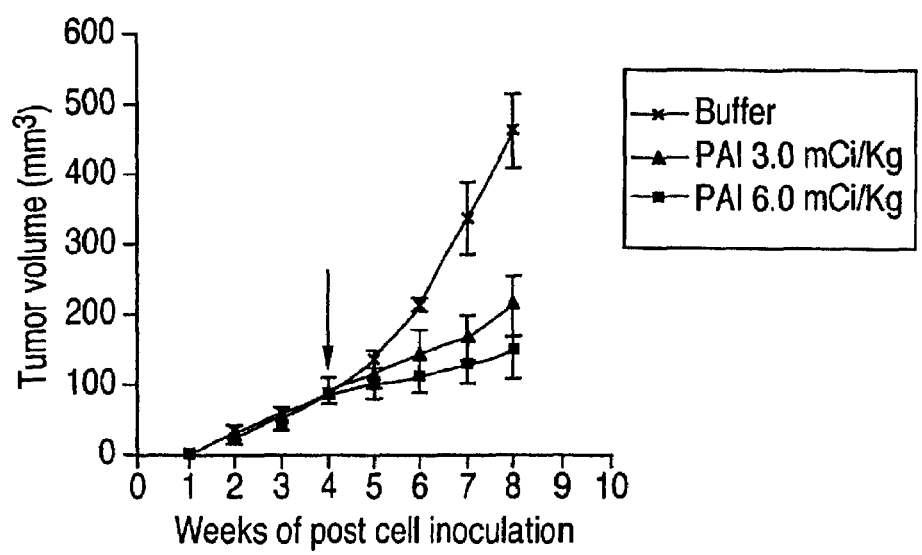
FIG. 15 Systemic TAT post tumor appearance in fourth week.

Alpha-PAI-2 (referred to as TAT in these instances) was inoculated intravenously (i.e. systemic administration) either 2 days (FIG. 13), 7 days (FIG. 14), or 4 weeks after PC-3 cell inoculation (FIG. 15). Each of these experiments contained 4 groups of 5 animals each, inoculated with a non-specific alpha-labelled antibody at 6 mCi/kg., or alpha-PAI-2 at 1.5 mCi/kg, 3 mCi/kg, or 6 mCi/kg. Each animal received a single injection of the drug, in 100 µl of solution.

At one week, the tumor volume was approximately 46 mm³, and at 4 weeks, the tumor volume was approximately 74 mm³. Tumour progression was documented by measuring volumes once weekly using calipers during the experiments, and their volumes were calculated by the following formula: length×width×height×0.52 in millimeters. Data points for both experiments were expressed as average tumor volume±SE of mean based on 4-7 determinations. The incidence of lymph node metastases is also reported, by observation. No mice died in these experiments.

Figure 13:
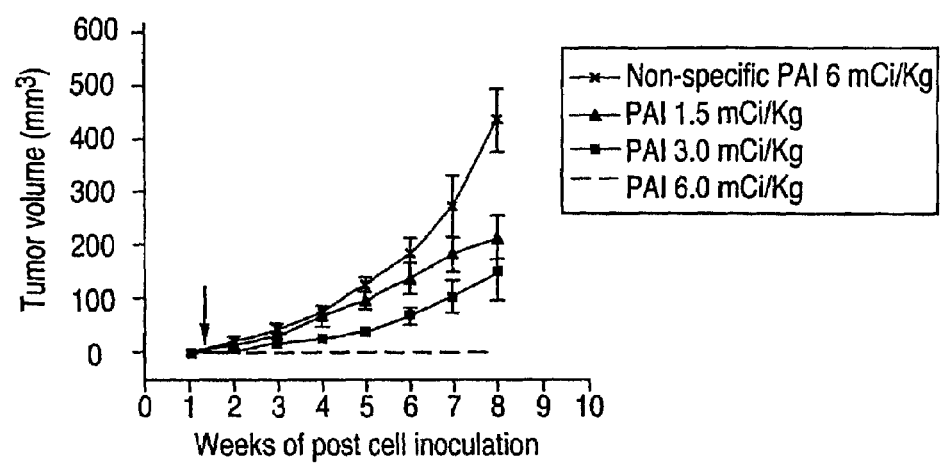
FIG. 13 Systemic TAT with PAI in PC-3 tumors after 2 days cell inoculation.

The results are presented in FIGS. 13, 14, and 15, and clearly show a dose related inhibition of prostate tumor cell growth in these animals, from the administration of alpha-PAI-2. The times of administration of alpha-PAI-2 by tail vein injection (i.v.) are indicated in these figures by an arrow. Similar results have been obtained from local administration of alpha-PAI-2 directly into the s.c. (sub-cutaneous) tumor.

EXAMPLE 7

Diagnostic Imaging of Cancer

Those skilled in the art will recognize that the same invention described herein can be used to identify the sites of tumors within the body.

Thus, PAI-2 can locate tumors which express uPA with high specificity, as described above. It follows that if the PAI-2 so used is labelled with any agent that can be detected, the tumor location can be visualized.

Examples of such detectable agents which could be coupled to PAI-2 include, but are not limited to, the following: radioactive Bi-213, as described in this application, which can be detected with any means of radioactive detection, such as a gamma camera; radioactive technetium (Tc-99m), similarly detected; or 18-fluoro labelling, which is detected by Positron Emission Tomography (PET).

The detection of sites of tumor growth has utility in the diagnosis of cancer, and in the identification of metastasis, that is, the spread of cancer from the primary tumor. It also has utility in defining the sites accessible for therapy, using any of the existing therapeutic modalities for cancer, including the alpha-PAI-2 described herein. The progression of cancer, and the effectiveness of treatment, can also be monitored using this PAI-2 targetting method for imaging of cancerous cells.

These data from the Examples above clearly demonstrate the imaging and anti-tumor effectiveness of the radio-conjugated PAI-2 molecules of the present invention.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The reference to any prior art in this specification is not, and should not be taken as, an acknowledgment or any form of suggestion that that prior art forms part of the common general knowledge in the field of endeavor.

BIBLIOGRAPHY

Allen, B. J. and Blagojevic, N. (1996) *Nuclear Medicine Communications* 17:40-47.

Allen, B. J. (1999) *Nuclear Medicine Communications* 20:205-207.

Andreasen, P. A., Kjoller, L., Christensen, L. and Duffy, M. J. (1997) *Int. J. Cancer* 72:1-22.
Bloomer, W. D. et al. (1984) *Int. J. Radiat. Oncol. Biol. Phys.* 10:341.
Duffy, M. J., Maguire, T. M., McDermott, E. W., et al. (1999) (*J. Surg. Oncol.* 71:130-135.
Gandolfo, G. M., Conti, L. and Vercillo, M. (1996) *Anticancer Res.* 16:2155-2159.
Gansow, O. A., Wu, C. (1995) Advanced methods of radiolabeling monoclonal antibodies with therapeutic radionuclides, Ed: Goldenberg D M, CRC Press. pp 63-76.
Foekens, J. A., Buessecker, F., Peters, H. A., et al. (1995) *Cancer Res.* 55:1423-1427.
Hang, M. T. H., Ranson, M., Saunders, D. N., Liang, X-M., Bunn, C. L. and Baker, M. S. (1998) *Fibrinol. Proteol.* 12:145-154.
Haber, D. A. and Fearon, E. R. (1998) *Lancet.* 351 (*suppl II*):1-8.
Horak, E., Hartmann, F., Garmestani, K. et al. (1997) *J. Nucl. Med.* 38:1944-1950.
Imam, S. K., Allen, B. J., Goozee, G., Sarkar, S. and Hersey, P. (1997) *Melanoma Res.* 7(1):S35.
Izard, M. et al. (1992) *Bioconjugate Chem.* 3:346-350.
Kassis, A. I., Harris, C. R., Adelstein, S. J. et al. (1986) *Radiat Res.* 105:27-36.
Kennel, S. J., Boll, R., Stabin, M., Schuller, H. M. and Mirzadeh, S. (1999) *Br. J. Cancer.* 80:175-184.
Kim, J., Yu, W., Kovalski, K. and Ossowski, L. (1998) *Cell.* 74:353-362.
Kruithof E. K. O., Baker, M. S., Bunn, C. L. (1995) *Blood.* 85:4007-4024.
Kueng, W., Silber, E. and Eppenberger, U. (1989) *Anal. Biochem.* 182:16-19.
Larsen, R. H., Akabani, G., Welsh, P., Zalutski, M. R. (1998) *Radiation Research.* 149:152-157.
Laug, W. E., Cao, X. R., Yu, Y. B. et al. (1993) *Cancer Res.* 53:6051-6057.
Lijnen, H. R. and Collen, D. (1982) *Sem. Thromb. Hemos.* 8:2-10.
Link, E. V., Michalowski, A. S., Rosch, F. (1994) *Pigment Cell Research.* 7:358-362.
Lloyd, E. L., Gemmell, M. A., Henning, C. B., Gemmell, D. S., Zabraqnaky, B. J. (1979) *Int. J. Radiat. Biol.* 35:123-132.
Macklis, R. M. et al. (1993) *Int. J. Oncol.* 2:711-715.
Meyer, T. and Hart, I. R. (1998) *E.J. Cancer.* 34:214-221.
Mohan, P. M. Chintala, S. K. Mohanam, S. et al. (1999) *Cancer Res.* 59:3369-73.
Mueller, B. A., Yu, Y. B., Laug, W. E. (1995) *Proc. Natl. Acad. Sci. USA* 92:205-209.
Pöllänen, J., Stephens, R., Vaheri, A. (1991) *Adv. Cancer Res.* 57:273-328.
Ranson, M. Andronicos, N. M., O Mullane, M. and Baker, M. S. (1998) *Br. J. Cancer.* 77:1586-1597.
Schmitt, M., Harbeck, N., Thomssen, C., Wilhelm, O., Magdolen, V., Reuning, U., Ulm, K., Hofler, H., Janicke, F. and Graeff, H. (1997) *Thromb-Haemost.* 78:285-296.
Yang, J. L., Seetoo, D., Wang, Y., Ranson, M., Berney, C. R., Ham, J. M., Russell, P. J. and Crowe, P. J. (1999) Urokinase-type plasminogen activator receptor (UPAR) in invasion and metastasis of human colorectal cancer. In: Proceedings of the 35th American Society of Clinical Oncology Annual Meeting. Vol. 18:243. (full paper submitted to. J. Clin. Onocol.).

The invention claimed is:

1. A PAI-2 conjugate molecule that is internalized by a cell that expresses a uPA/uPAR complex, said molecule comprising a component (i) that is PAI-2 and, bound or linked via a chelator thereto, a component (ii) that is a radioisotope, wherein component (i) binds to uPA.

2. The PAI-2 conjugate of claim 1, wherein the radioisotope is an alpha particle emitting radioisotope.

3. The PAI-2 conjugate of claim 2, wherein the alpha particle emitting radioisotope is Tb-149 or Bi-213.

4. The PAI-2 conjugate of claim 1, wherein the PAI-2 conjugate molecule is selected from the group consisting of
Tb-149.cDTPA.PAI-2,
Tb-149.CHX.PAI-2,
Bi-213.cDTPA.PAI-2 and
Bi-213.CHX.PAI-2.

5. The PAI-2 conjugate of claim 1, wherein the radioisotope is a gamma ray emitting particle.

6. The PAI-2 conjugate of claim 5, wherein the gamma ray emitting particle is technetium (Tc-99m).

7. The PAI-2 conjugate of claim 1, wherein the radioisotope is F-18, which is detectable by Position Emission Tomography (PET).

8. The PAI-2 conjugate of claim 1, wherein said chelator is selected from the group consisting of cDTPA, CHX-A, DOTA and TETA.

9. A pharmaceutical composition comprising one or more pharmaceutically acceptable carriers and/or diluents and a PAI-2 conjugate molecule that is internalized by a cell that expresses a uPA/uPAR complex, wherein said PAI-2 conjugate molecule comprises a component (i) that is PAI-2 and, bound or linked via a chelator thereto, a component (ii) that is a radioisotope, wherein component (i) binds to uPA.

10. The pharmaceutical composition of claim 9, wherein the pharmaceutical composition is formulated for intravenous or subcutaneous application.

11. The pharmaceutical composition of claim 9, wherein the radioisotope is an alpha particle emitting radioisotope.

12. The pharmaceutical composition of claim 11, wherein the alpha particle emitting radioisotope is Tb-149 or Bi-213.

13. The pharmaceutical composition of claim 9, wherein the PAI-2 conjugate molecule is selected from the group consisting of
Tb-149.cDTPA.PAI-2,
Tb-149.CHX.PAI-2,
Bi-213.cDTPA.PAI-2 and
Bi-213.CHX.PAI-2.

14. The pharmaceutical composition of claim 9, wherein the radioisotope is a gamma ray emitting particle.

15. The pharmaceutical composition of claim 14, wherein the gamma ray emitting particle is technetium (Tc-99m).

16. The pharmaceutical composition of claim 9, wherein the radioisotope is F-18, which is detectable by Position Emission Tomography (PET).

17. The pharmaceutical composition of claim 9, wherein said chelator is selected from the group consisting of cDTPA, CHX-A, DOTA and TETA.

* * * * *